United States Patent
Bothfeld et al.

(10) Patent No.: US 12,168,679 B2
(45) Date of Patent: Dec. 17, 2024

(54) MODIFIED BACTERIA FOR ENHANCED BIOPRODUCTION AND METHODS OF USING THE SAME

(71) Applicant: Northwestern University, Evanston, IL (US)

(72) Inventors: William H. Bothfeld, Chicago, IL (US); Keith E. J. Tyo, Evanston, IL (US)

(73) Assignee: Northwestern University, Evanston, IL (US)

(*) Notice: Subject to any disclaimer, the term of this patent is extended or adjusted under 35 U.S.C. 154(b) by 0 days.

(21) Appl. No.: 17/522,441

(22) Filed: Nov. 9, 2021

(65) Prior Publication Data

US 2022/0144899 A1    May 12, 2022

Related U.S. Application Data

(60) Provisional application No. 63/111,851, filed on Nov. 10, 2020.

(51) Int. Cl.
| | |
|---|---|
| C07K 14/245 | (2006.01) |
| C12N 15/70 | (2006.01) |
| C12P 5/00 | (2006.01) |
| C12P 7/42 | (2006.01) |

(52) U.S. Cl.
CPC ............ C07K 14/245 (2013.01); C12N 15/70 (2013.01); C12P 5/002 (2013.01); C12P 7/42 (2013.01)

(58) Field of Classification Search
CPC ....... C07K 14/245; C12N 15/70; C12P 5/002; C12P 7/42; C12P 1/04; C12P 5/007
See application file for complete search history.

(56) References Cited

U.S. PATENT DOCUMENTS 9,902,965 B2    2/2018    Blattner et al.

OTHER PUBLICATIONS

Whisstock et al. Quaterly Reviews of Biophysics, 2003, "Prediction of protein function from protein sequence and structure", 36(3):307-340. (Year: 2003).*
Witkowski et al. Conversion of a beta-ketoacyl synthase to a malonyl decarboxylase by replacement of the active-site cysteine with glutamine, Biochemistry. Sep. 7, 1999;38(36):11643-50. (Year: 1999).*
Kisselev L., Polypeptide release factors in prokaryotes and eukaryotes: same function, different structure. Structure, 2002, vol. 10:8-9. (Year: 2002).*
Amitai et al. MazF-mediated cell death in *Escherichia*: a point of no return. J Bacteriol (2004): 186(24): 8295-8300. (Year: 2004).*
Pedersen et al. Multiple hok genes on the chromosome of *Escherichia coli*. Molecular Microbiology (1999), 32(5); 1090-1102). (Year: 1999).*
Masuda et al. Toxins of prokaryotic toxin-antitoxin systems with sequence-specific endoribonuclease activity. Toxins (2017), 140: p. 1-23. (Year: 2017).*
Polikanov et al. How hibernation factors RMF, HPF and YfiA turn off protein synthesis. Science (2012), 336(6083): 915-918. (Year: 2012).*
Lusetti et al. C-terminal deletions of the *Escherichia coli* RecA protein characterization of in vivo and in vitro effects. JBC (2003), 278(18): 16372-16380. (Year: 2003).*
Zhu et al. Enhancing 5-aminolevulinic acid tolerance and production by engineering the antioxidant defense system of *Escherichia coli*. Biotechnology Bioengineering (2019), 116:2018-2028. (Year: 2019).*
Egbert et al. A versatile platform strain for high-fidelity multiplex genome editing. Nucleic Acids Research (2019), 47(6): 3244-3256. (Year: 2019).*
Tsilibaris et al. What is the benefit to *Escherichia coli* of having multiple toxin-antitoxin systems in its genome? J Bacteriol (2007): 189(17): 6101-6108. (Year: 2007).*
Goormaghtigh et al. (Reassessing the role of Type II Toxin-Antitoxin systems in formation of *Escherichia coli* Type II persister cells. mBio (2018), 9(3): 1-14). (Year: 2018).*
Maisonneuve et al. (Bacterial persistence by RNA endonucleases. PNAS (2011), 108(32): 13206-13211). (Year: 2011).*
Nazia Koser Zaman (An investigation of Type I toxin-antitoxin systems from *E. coli*. Master Thesis, Norwegian University of Life Sciences, Faculty of Veterinary Medicine and Biosciences, Department of Chemistry, Biotechnology and Food Science, (2015), p. 1-124). (Year: 2015).*
Alonso-Gutierrez et al., "Metabolic engineering of *Escherichia coli* for limonene and perillyl alcohol production," Metabolic Engineering, Sep. 2013, 19:33-41.
Alonso-Gutierrez et al., "Principal component analysis of proteomics (PCAP) as a tool to direct metabolic engineering," Metabolic Engineering, Mar. 2015, 28:123-133.
Brunk et al., "Characterizing strain variation in engineered *E. coli* using a multi-omics based workflow," Cell Syst., May 25, 2016, 2(5):335-346.
Juminaga et al., "Modular engineering of L-Tyrosine Production in *Escherichia coli*," Applied and Environmental Microbiology, Jan. 2012, 78(1):89-98.

* cited by examiner

*Primary Examiner* — Iqbal H Chowdhury
(74) *Attorney, Agent, or Firm* — Foley & Lardner LLP

(57) ABSTRACT

The present disclosure relates generally to modified bacteria, such as *E. coli*, with modification in the expression of at least one gene encoding a type I and/or type II toxin-antitoxin (TA) system protein and/or at least one gene encoding a structural protein that modulates ribosomes and methods of using the disclosed bacteria for producing a biological compound of interest. The modifications of the bacteria result in enhanced bioproduction.

25 Claims, 8 Drawing Sheets

| ES | Genotype |
|---|---|
| 1 | ΔmazF ΔchpB ΔrelBE ΔyefM |
| 2 | ΔdinJ ΔhigBA ΔprlF ΔyafNO ΔmqsRA ilvG+ |
| 3 | ΔhipA |
| 4 | ΔrelA |
| 5 | ΔhipA ΔrelA |
| 6 | ΔhipA Δrsfs |
| 7 | ΔhipA Δrmf |
| 8 | ΔhipA Δhpf |
| 9 | ΔhipA ΔelaB |
| 10 | ΔhipA ΔyqjD |
| 11 | ΔhipA Δrmf Δhpf ΔrecA |
| 12 | ΔhipA Δrmf Δhpf Δrsfs |
| 13 | ΔhipA Δrmf Δhpf ΔraiA |
| 14 | ΔhipA Δrmf Δhpf ΔraiA Δrsfs |
| 15 | ΔhipA Δrmf Δhpf ΔraiA Δrsfs ΔSRA |
| 16 | ΔhipA Δrmf Δhpf ΔraiA Δrsfs ΔrecA |
| 17 | ΔhipA Δrmf Δhpf ΔraiA ΔyqjD |
| 18 | ΔhipA Δrmf Δhpf ΔraiA ΔyqjD ΔhokB |
| 19 | ΔhipA Δrmf Δhpf ΔraiA ΔyqjD ΔelaB |
| 20 | ΔhipA Δrmf Δhpf ΔraiA ΔyqjD ΔelaB ΔhokB ΔrecA |
| 21 | ΔhipA Δrmf Δhpf ΔraiA ΔyqjD ΔelaB ΔhokB ΔrecA ΔygaM |

Fig. 9

MODIFIED BACTERIA FOR ENHANCED BIOPRODUCTION AND METHODS OF USING THE SAME

CROSS-REFERENCE TO RELATED PATENT APPLICATIONS

This application claims priority under 35 U.S.C. § 119(e) to U.S. Provisional Patent Application No. 63/111,851, filed Nov. 10, 2020, the entire contents of which are incorporated herein by reference.

STATEMENT REGARDING FEDERALLY SPONSORED RESEARCH OR DEVELOPMENT

This invention was made with government support under grant number 1452549 awarded by the National Science Foundation (NSF). The government has certain rights in the invention.

FIELD OF INVENTION

The present disclosure relates generally to modified bacteria, such as *E. coli*, with modification in the expression of at least one gene encoding a type I and/or type II toxin-antitoxin (TA) system protein and/or at least one gene encoding a structural protein that modulates ribosomes and methods of using the disclosed bacteria for producing a biological compound of interest. The modifications of the bacteria result in enhanced bioproduction.

BACKGROUND

The following discussion is merely provided to aid the reader in understanding the disclosure and is not admitted to describe or constitute prior art thereto.

Renewable biochemical production using reprogramming biology is an exciting possibility to reduce anthropomorphic carbon emissions, among other commercial benefits. However, biology is rarely able to produce value-added molecules without substantial engineering of native metabolism and introduction of heterologous enzymes and pathways. The long time scales and high risks associated with engineering a productive strain have been identified as key challenges to enabling bioprocesses to achieve commercially relevant scales and titers.

A variety of tools and strategies have been developed to engineer biology, but they have primarily focused on the metabolic enzymes themselves. First generation metabolic engineering techniques altered flux through pathways by gene deletion, disruption, or overexpression. More recently the field has been interested in fine-tuning enzyme levels with promoter libraries or inducible expression systems to balance pathways. Further pathway flux increases were pursued by testing new enzymes and editing cellular metabolism. Superior enzymes were found by bioprospecting for enzyme homologues using sequence mining tools or by generating large enzyme libraries through PCR or cheap DNA synthesis. In parallel, strain improvements were identified by manual inspection of metabolism or through predictions from computational models that often are non-intuitive.

Typically, numerous genetic changes are suggested, and multiplexed strain-editing techniques allow combinatorial generation of strain diversity at multiple gene locations, with sequence diversity at each site. Optimized pathway enzymes and productive strains can be isolated using high-throughput selection pipelines by coupling product synthesis to cell-growth or product tolerance. However, creating effective screens remains a major challenge because desirable phenotypes are not always growth- or tolerance-associated, which creates a bottleneck in the pathway improvement pipeline. Techniques to rapidly prototype and screen pathways, such as cell-free synthesis, phage-assisted evolution, or droplet-based screens that tie phenotype and genotype to a biosensor, have shown some promise, but these techniques are nevertheless resource intensive and the genetic diversity sampled is still only a small portion of the possible protein design space.

Second generation strategies to program biology and create new metabolic pathways from scratch are also theoretically promising, but of limited success in practice. Efforts include: (1) de novo design of proteins with unique chemistries and spatial co-localization to pathway constituents, (2) design of alternative metabolic pathways that are more thermodynamically favorable, (3) design of autonomously activated pathways that have dynamic feedback control for flux balance to minimize cell stress, and (4) design of new culture strategies that decouple growth and production phases, which enables edits to essential genes and synthesis of products toxic to growth. These efforts may be helpful in eventually enabling longer, more complex heterologous pathways to reach commercially viable productivities, but as with other techniques, designs are imperfect and current limitations include fully integrating experimental data into models to improve the design process.

Even with all these new tools, the field has seen limited commercial success of complex biochemical production platforms, and promising results at bench scale often do not translate upon scale-up to pilot project size demonstrations.

Accordingly, there remains a need for a stable and efficient bacteria-based bioproduction system. The present disclosure satisfies this need.

SUMMARY

The present disclosure provides a stable and efficient bacteria-based bioproduction system. The disclosed bacteria have been modified to reduce or remove expression of one or more stress response effector proteins in order to enhance bioproduction of desirable chemicals and products.

In one aspect, the disclosure provides modified bacteria comprising a modification to the expression of at least one gene encoding a type I and/or type II toxin-antitoxin (TA) system protein and/or at least one gene encoding a structural protein that modulates ribosomes, wherein the modification reduces the activity of a toxin protein or suppresses the effects of a toxin protein.

In some embodiments of this aspect, the TA system protein is a type II TA system protein. In some embodiments of this aspect, the TA system protein is a type I TA system protein. In some embodiments of this aspect, a gene encoding a type I TA system protein and a gene encoding a type II TA system protein are both modified. In some embodiments of this aspect, at least one gene encoding a type I and/or type II TA system protein and at least one gene encoding a structural protein that modulates ribosomes are both modified.

In some embodiments of this aspect, the modification comprises a down regulation, mutation, or deletion of the gene.

In some embodiments of this aspect, the bacteria comprises a modification to the expression of at least 2, at least 3, at least four, at least 5, at least 6, at least 7, at least 8, at least 9, at least 10, or at least 11 genes encoding a TA system protein and at least one, at least two, at least three, or at least four gene(s) encoding a structural protein that modulates ribosomes.

In some embodiments of this aspect, the bacteria is *Escherichia coli* (*E. coli*).

In some embodiments of this aspect, at least 4 (Δ4TA), at least 5 (Δ5TA), at least 6 (Δ6TA), at least 7 (Δ7TA), at least 8 (Δ8TA), at least 9 (Δ9TA), at least 10 (Δ10TA), or at least 11 (Δ11TA) genes encoding TA system proteins are deleted.

In some embodiments of this aspect, the at least one gene encoding a type II TA system protein is selected from mazF (ΔmazF), chpB (ΔchpB), chpBS (ΔchpBS), relBE (ΔrelBE), yefM/yoeB (ΔyefM/yoeB), dinJ (ΔdinJ), yafQ (ΔyafQ), dinJ-yafQ (ΔdinJ-yafQ), yefM (ΔyefM), yoeB (ΔyoeB), higBA (ΔhigBA), prlF (ΔprlF), yhaV (ΔyhaV), prlF-yhaV (ΔprlF-yhaV), yafNO (ΔyafNO), mqsRA (ΔmqsRA), hicAB (ΔhicAB), hip BA (ΔhipA), and yaNOP (ΔyaNOP).

In some embodiments of this aspect, the at least one gene encoding a type I TA system protein is selected from tisB (ΔtisB), hokB (ΔhokB), ibsAB (ΔibsAB), ibsCE (ΔibsCE), ldrABCD (ΔldrABCD), hokACDE (ΔhokACDE), ghoTS (ΔghoTS), cbtAB (ΔcbtAB), cptAB (ΔcptAB), shoB (ΔshoB), dinQ (ΔdinQ), symER (ΔsymER), and ralAR (ΔralAR). In some embodiments of this aspect, at least one, at least two, or all three of hokB, tisB, and shoB are knocked out.

In some embodiments of this aspect, mazEFG operon is deleted.

In some embodiments of this aspect, at least 2, at least 3, at least 4, at least 5, or at least 6 genes encoding a structural protein that modulates ribosomes are deleted. In some embodiments of this aspect, the genes encoding a structural protein that modulates ribosomes are selected from rmf (Δrmf), hpf (Δhpf), rsfs (Δrsfs), yqjD (ΔyqjD), elaB (ΔelaB), raiA (ΔraiA), ygaM (ΔygaM), and SRA (ΔSRA).

In some embodiments of this aspect, the bacteria comprises Δ11TA and/or ΔhpfΔrmf. In some embodiments of this aspect, the bacteria comprises Δ11TA and ΔhpfΔrmf. In some embodiments of this aspect, the bacteria comprises Δ11TA and ΔhpfΔrmfΔraiAΔrsfsΔSRA. In some embodiments of this aspect, the bacteria comprises ΔhpfΔrmfΔraiAΔrsfsΔSRA. In some embodiments of this aspect, the bacteria comprises Δ11TA and ΔhpfΔrmfΔraiAΔyqjDΔelaBΔygaM. In some embodiments of this aspect, the bacteria comprises ΔhpfΔrmfΔraiAΔyqjDΔelaBΔygaM. In some embodiments of this aspect, the bacteria comprises Δ11TA and ΔhpfΔrmf and further comprises any of the following deletions: Δrsfs, ΔraiA, ΔSRA, ΔyqjD, Δelab, ΔygaM, ΔrelA, or ΔrecA. In some embodiments of this aspect, the bacteria comprises ΔhpfΔrmf and further comprises any of the following deletions: Δrsfs, ΔraiA, ΔSRA, ΔyqjD, Δelab, ΔygaM, ΔrelA, or ΔrecA. In some embodiments of this aspect, the bacteria comprises Δ11TA and ΔhpfΔrmfΔrecAΔrelA. In some embodiments of this aspect, the bacteria comprises ΔhpfΔrmfΔrecAΔrelA.

In some embodiments of this aspect, relA is deleted (ΔrelA).

In some embodiments of this aspect, recA is deleted (ΔrecA).

In some embodiments of this aspect, an ilvG− frameshift mutation is corrected (ilvG+).

Some embodiment of this aspect may further comprise one or more modifications to alter expression of katG and/or sodB.

Some embodiments of this aspect may further comprise one or more modifications to up- or down-regulate at least one general stress gene, at least one cold shock gene, at least one osmotic shock gene, or at least one heat shock gene, and remove at least one flagellar gene. In some embodiments of this aspect, the at least one flagellar gene is fliDST, fhBAE, cheRABZYW, tar, tsr, trg, or tap.

Some embodiments of this aspect may further comprise one or more modifications to down regulate or remove at least one gene relating to biofilm production, curli, fimbrae, cellulose, or adhesins. In some embodiments of this aspect, the at least one gene relating to biofilms is hna, tabA, or wcaF. In some embodiments of this aspect, the at least one gene relating to curli is csgBA and/or csgDEFG. In some embodiments of this aspect, the at least one gene relating to fimbrae is fim operon, aidA, or tibA. In some embodiments of this aspect, the at least one gene relating to cellulose is bcsE or dgcC. In some embodiments of this aspect, the at least one gene relating to adhesins is yad, bfp, pap, or tpsA.

In some embodiments of this aspect, the bacteria has been modified to alter genes involved in di-cyclic GTP signaling.

In some embodiments of this aspect, the bacteria has not been modified to alter genes involved in di-cyclic GTP signaling.

In another aspect, the disclosure provides modified bacteria comprising one or more modifications to the expression of at least one flagellar gene; at least one gene relating to biofilm production, curli, fimbrae, cellulose, or adhesins; at least one gene involved in di-cyclic GTP signaling; or a combination thereof.

In some embodiments of this aspect, the at least one flagellar gene is fliDST, flhBAE, cheRABZYW, tar, tsr, trg, or tap. In some embodiments of this aspect, the at least one gene relating to biofilms is hna, tabA, or wcaF. In some embodiments of this aspect, the at least one gene relating to curli is csgBA and/or csgDEFG. In some embodiments of this aspect, the at least one gene relating to fimbrae is fim operon, aidA, or tibA. In some embodiments of this aspect, the at least one gene relating to cellulose is bcsE or dgcC. In some embodiments of this aspect, the at least one gene relating to adhesins is yad, bfp, pap, or tpsA.

In some embodiments of this aspect, the modification relates to the expression of at least one flagellar gene. In some embodiments of this aspect, the modification relates to the expression of at least one gene relating to biofilm production, curli, fimbrae, cellulose, or adhesins. In some embodiments of this aspect, the modification relates to the expression of at least one gene involved in di-cyclic GTP signaling. In some embodiments of this aspect, the modification relates to the expression of at least two of: a flagellar gene; a gene relating to biofilm production, curli, fimbrae, cellulose, or adhesins; and a gene involved in di-cyclic GTP signaling. In some embodiments of this aspect, the modification relates to the expression of all three of: at least one flagellar gene; at least one gene relating to biofilm production, curli, fimbrae, cellulose, or adhesins; and at least one gene involved in di-cyclic GTP signaling.

In some embodiments of this aspect, the one or more modifications comprise an up-regulation or down-regulation of the gene(s). In some embodiments of this aspect, the one or more modifications comprise a down regulation, mutation, or deletion of the gene.

Some embodiments of this aspect may further comprise a modification to the expression of at least one gene encoding a type I and/or type II toxin-antitoxin (TA) system protein and/or at least one gene encoding a structural protein that modulates ribosomes, wherein the modification reduces the activity of a toxin protein or suppresses the effects of a toxin protein. In some embodiments of this aspect, the TA system protein is a type II TA system protein. In some embodiments of this aspect, the TA system protein is a type I TA system protein. In some embodiments of this aspect, a gene encoding a type I TA system protein and a gene encoding a type II TA system protein are both modified. In some embodiments of this aspect, at least one gene encoding a type I and/or type II TA system protein and at least one gene encoding a structural protein that modulates ribosomes are both modified.

In some embodiments of this aspect, the bacteria comprises a modification to the expression of at least 2, at least 3, at least four, at least 5, at least 6, at least 7, at least 8, at least 9, at least 10, or at least 11 genes encoding a TA system protein and at least one, at least two, at least three, or at least four gene(s) encoding a structural protein that modulates ribosomes.

In some embodiments of this aspect, at least 4 (Δ4TA), at least 5 (Δ5TA), at least 6 (Δ6TA), at least 7 (Δ7TA), at least 8 (Δ8TA), at least 9 (Δ9TA), at least 10 (Δ10TA), or at least 11 (Δ11TA) genes encoding TA system proteins are deleted.

In some embodiments of this aspect, the at least one gene encoding a type II TA system protein is selected from mazF (ΔmazF), chpB (ΔchpB), chpBS (ΔchpBS), relBE (ΔrelBE), yefM/yoeB (ΔyefM/yoeB), dinJ (ΔdinJ), yafQ (ΔyafQ), dinJ-yafQ (ΔdinJ-yafQ), yefM (ΔyefM), yoeB (ΔyoeB), higBA (ΔhigBA), prlF (ΔprlF), yhaV (ΔyhaV), prlF-yhaV (ΔprlF-yhaV), yafNO (ΔyafNO), mqsRA (ΔmqsRA), hicAB (ΔhicAB), hip BA (ΔhipA), and yafNOP (ΔyafNOP).

In some embodiments of this aspect, the at least one gene encoding a type I TA system protein is selected from tisB (ΔtisB), hokB (ΔhokB), ibsAB (ΔibsAB), ibsCE (ΔibsCE), ldrABCD (ΔldrABCD), hokACDE (ΔhokACDE), ghoTS (ΔghoTS), cbtAB (ΔcbtAB), cptAB (ΔcptAB), shoB (ΔshoB), dinQ (ΔdinQ), symER (ΔsymER), and ralAR (ΔralAR). In some embodiments of this aspect, at least one, at least two, or all three of hokB, tisB, and shoB are knocked out.

In some embodiments of this aspect, at least 2, at least 3, at least 4, at least 5, or at least 6 genes encoding a structural protein that modulates ribosomes are deleted. In some embodiments of this aspect, the genes encoding a structural protein that modulates ribosomes are selected from rmf (Δrmf), hpf (Δhpf), rsfs (Δrsfs), yqjD (ΔyqjD), elaB (ΔelaB), raiA (ΔraiA), ygaM (ΔygaM), and SRA (ΔSRA).

In some embodiments of this aspect, the bacteria comprises Δ11TA and/or ΔhpfΔrmf. In some embodiments of this aspect, the bacteria comprises Δ11TA and ΔhpfΔrmf. In some embodiments of this aspect, the bacteria comprises Δ11TA and ΔhpfΔrmfΔraiAΔrsfsΔSRA. In some embodiments of this aspect, the bacteria comprises ΔhpfΔrmfΔraiAΔrsfsΔSRA. In some embodiments of this aspect, the bacteria comprises Δ11TA and ΔhpfΔrmfΔraiAΔyqjDΔelaBΔygaM. In some embodiments of this aspect, the bacteria comprises ΔhpfΔrmfΔraiAΔyqjDΔelaBΔygaM. In some embodiments of this aspect, the bacteria comprises Δ11TA and ΔhpfΔrmf and further comprises any of the following deletions: Δrsfs, ΔraiA, ΔSRA, ΔyqjD, Δelab, ΔygaM, ΔrelA, or ΔrecA. In some embodiments of this aspect, the bacteria comprises ΔhpfΔrmf and further comprises any of the following deletions: Δrsfs, ΔraiA, ΔSRA, ΔyqjD, Δelab, ΔygaM, ΔrelA, or ΔrecA. In some embodiments of this aspect, the bacteria comprises Δ11TA and ΔhpfΔrmfΔrecAΔrelA. In some embodiments of this aspect, the bacteria comprises ΔhpfΔrmfΔrecAΔrelA.

In some embodiments of this aspect, mazEFG operon is deleted.

In some embodiments of this aspect, relA is deleted (ΔrelA).

In some embodiments of this aspect, recA is deleted (ΔrecA).

In some embodiments of this aspect, an ilvG– frameshift mutation is corrected (ilvG+).

Some embodiments of this aspect may further comprise one or more modifications to alter expression of katG and/or sodB.

In some embodiments of this aspect, the bacteria is *Escherichia coli* (*E. coli*).

In another aspect, the present disclosure provides methods of producing a compound of interest in a modified bacteria, comprising culturing a modified bacteria according to any one of the foregoing aspect or embodiments, which also expresses or produces an exogenous compound of interest.

In some embodiments, the exogenous compound of interest is selected from the group consisting of a protein, mevalonate, a terpene, an amino acid, an organic acid, muconate or cis,cis-muconic acid, a fatty acid, amorphadiene, artemisinic acid, a diol, and shikimate. In some embodiments, the terpene is limonene, amorphadiene, taxadiene, bisabolene, famesene, or pinene. In some embodiments, the amino acid is tyrosine. In some embodiments, the organic acid is citric acid, succinic acid, or 3-hydroxypropionic acid. In some embodiments, the diol is 1,4-butanediol or 1,3-propanediol.

In some embodiments, the exogenous compound of interest is selected from hydroxyl-tyrosine and butanol The foregoing general description and following detailed description are exemplary and explanatory and are intended to provide further explanation of the disclosure as claimed. Other objects, advantages, and novel features will be readily apparent to those skilled in the art from the following brief description of the drawings and detailed description of the disclosure.

BRIEF DESCRIPTION OF DRAWINGS

FIG. 9 (FIG. 9) shows a key that indicates the genotype of each of the ES strains (e.g., ES1, ES2, ES3, ES4, etc.) utilized in Example 4 and indicated in FIGS. 6-8.

DETAILED DESCRIPTION

Figure 1:
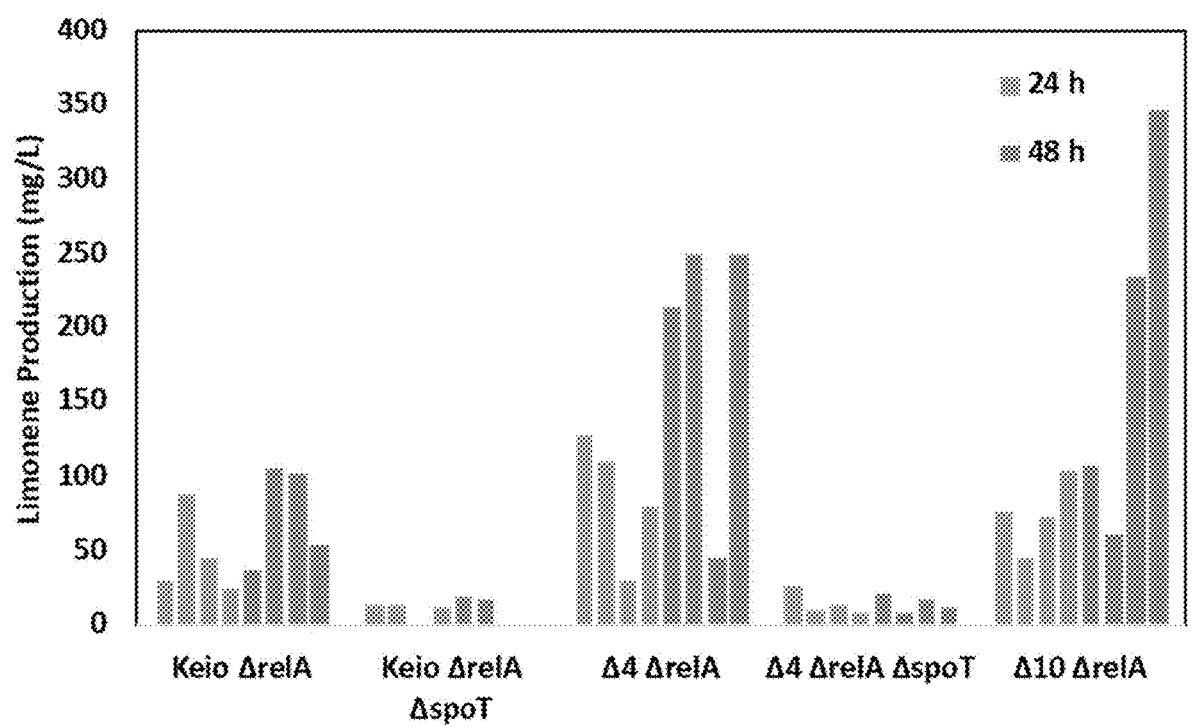
FIG. 1 (FIG. 1) shows limonene production in relaxed response strains.
Figure 2:
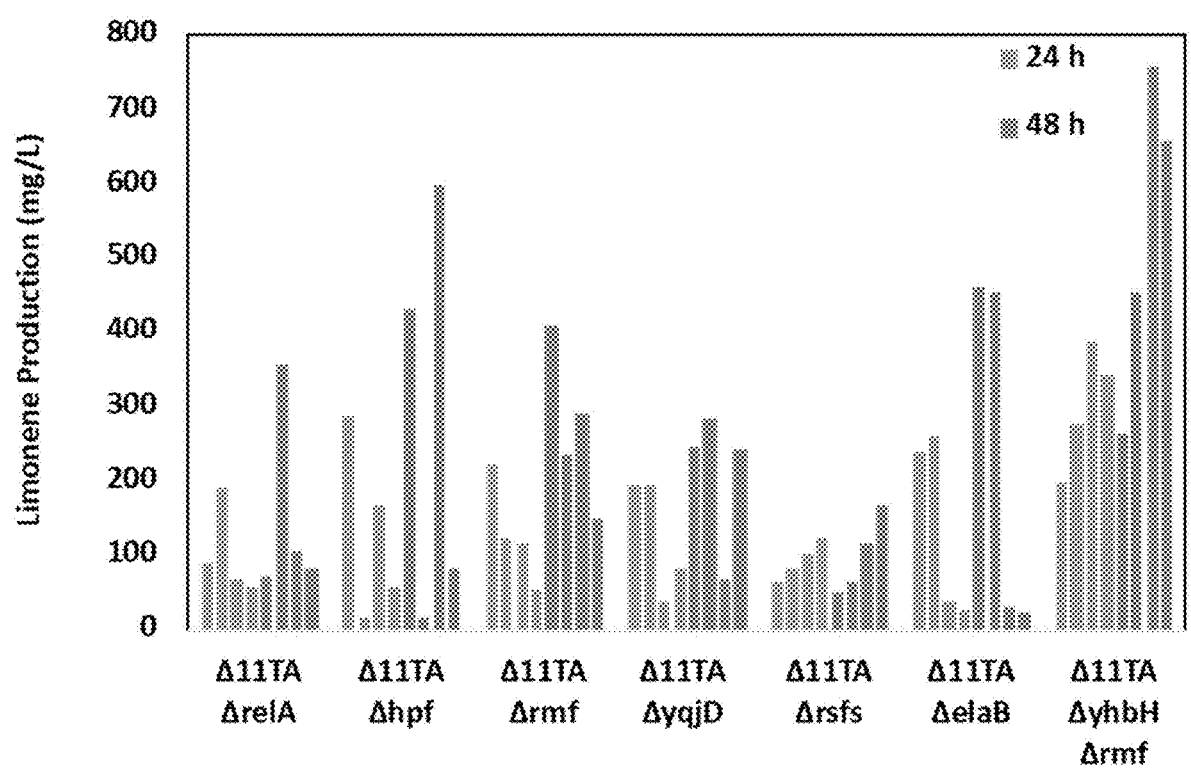
FIG. 2 (FIG. 2) shows improved limonene production in stringent response effector strains lacking 100S ribosomal hibernation factors.
Figure 3:
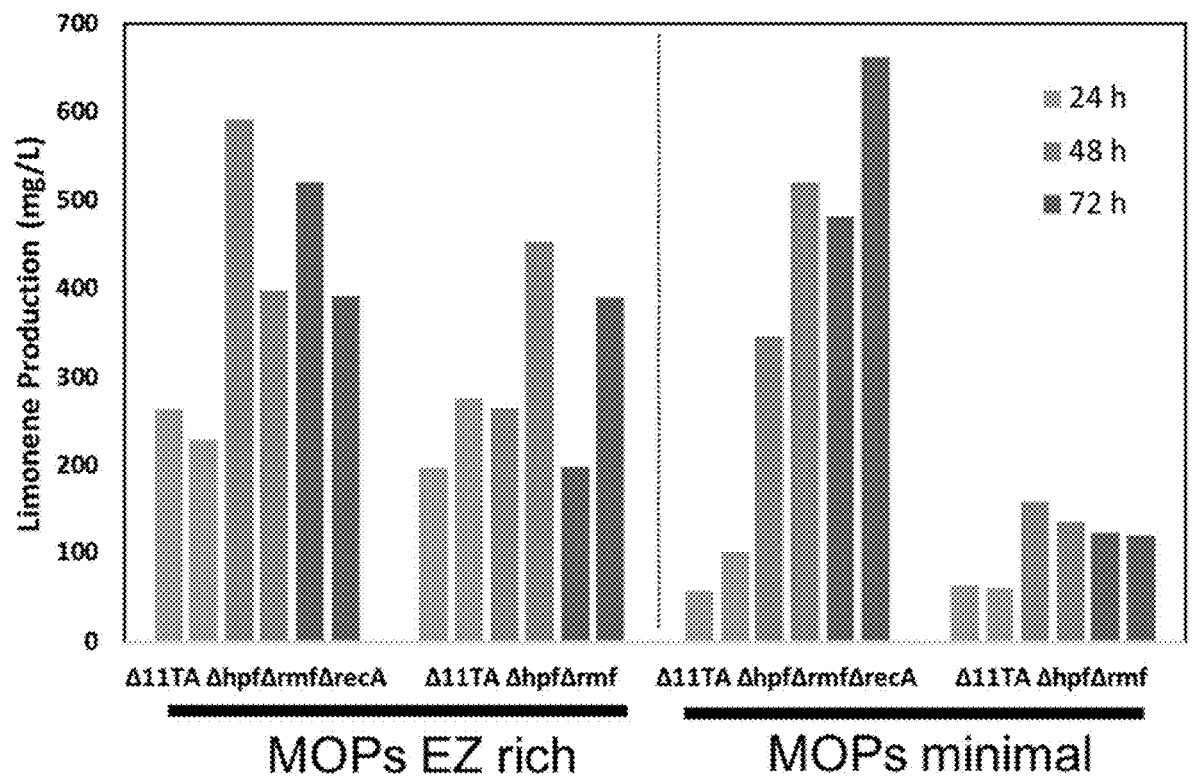
FIG. 3 (FIG. 3) shows high limonene production in minimal media in a strain lacking recombination machinery. A ΔrecA strain produces high limonene titers in rich and minimal media as compared to a strain with wildtype recA.

Efforts to engineer bacteria, such as *Escherichia coli* (*E. coli*), for biochemical and chemical production often result in heavily optimized but fragile strains that can dramatically lose productivity due to modest changes in environment or further engineering. Engineering changes cause stress from the overproduction of heterologous enzymes, introduction of foreign metabolites, and the perturbation of native metabolite pools. This stress may activate multiple redundant cellular response programs that shutdown metabolism to hibernate the cell to minimize further stress. Previous engineering efforts have sought to balance pathways, while operating only a small perturbation away from metabolic shutdown.

Rather than operate near the stress response state, the present disclosure provides a way to attenuate the stress response by rationally and systematically removing stress response effector proteins, while maintaining the stress sensing network. This generates robust chassis strains that exhibit improved biochemical production without pathway-specific engineering. The disclosed strains were benchmarked using an off-the-shelf limonene pathway as a strict test case due to known toxicities from pathway intermediates, product, and enzyme overproduction. Indeed, limonene titers were improved by 75% to a high of ~760 mg/L using established process conditions (e.g., those disclosed in Alonso-Gutierrez et al., *Metabolic engineering of Escherichia coli for limonene and perillyl alcohol production*, Metab. Eng., 19:33-41 (2013)) and a ~25% improvement compared to follow-up optimization efforts. These improvements were consistent in minimal media with a high of 660 mg/L, which will drastically reduce bioprocessing costs.

Accordingly, the disclosed chassis strains will substantially simplify the development pipeline for the bioprocessing of compounds of interest (e.g., commercially valuable biochemical and chemicals), as the strains do not unnecessarily induce a stress response due to metabolic engineering. These strains will facilitate the move toward a fully renewable bio-economic future.

Various patent application publications, patents, journal articles, and/or books may be referenced throughout the course of this disclosure. These references are not admitted to describe or constitute prior art, but are incorporated by reference herein in their entirety.

I. Definitions

It is to be understood that the disclosed compositions and methods are not limited to the particular embodiments described, and as such may vary. It is also to be understood that the terminology used herein is for the purpose of describing particular embodiments only, and is not intended to be limiting. The scope of the present technology will be limited only by the appended claims.

As used herein, certain terms may have the following defined meanings. As used in the specification and claims, the singular form "a," "an" and "the" include singular and plural references unless the context clearly dictates otherwise. For example, the term "a cell" includes a single cell as well as a plurality of cells, including mixtures thereof.

As used herein, "about" means the recited quantity exactly and plus or minus 10%. For example, "about 10" should be understood to mean "10" and "9-11".

As used herein, the term "comprising" is intended to mean that the compositions and methods include the recited elements, but not excluding others. "Consisting essentially of" when used to define compositions and methods, shall mean excluding other elements of any essential significance to the composition or method. "Consisting of" shall mean excluding more than trace elements of other ingredients for claimed compositions and substantial method steps. Embodiments defined by each of these transition terms are within the scope of this disclosure. Accordingly, it is intended that the methods and compositions can include additional steps and components (comprising) or alternatively including steps and compositions of no significance (consisting essentially of) or alternatively, intending only the stated method steps or compositions (consisting of).

As used herein, "optional" or "optionally" means that the subsequently described event or circumstance may or may not occur, and that the description includes instances where said event or circumstance occurs and instances where it does not.

For the purpose of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B, and C).

The description may use the terms "embodiment" or "embodiments," which may each refer to one or more of the same or different embodiments.

As used herein, "relaxed response strain" means a bacterial strain that comprises at least the ΔrelA edit.

As used herein, "stringent response effector strain" means a bacterial strain that comprises at least one modification to down regulation or prevent expression of at least one gene encoding a toxin-antitoxin (TA) system protein (e.g., a type I or type II TA system protein) or any regulation that is downstream of ppGpp/stringent response (e.g., hibernation response [hpf/rmf]).

II. Modified Bacteria Strains

Biological engineering (i.e., "recombineering") of bacterial strains that can be used for bioproduction of chemicals, biochemicals, and other desirable compounds often results in fragile biocatalysts. A typical strain development plan primarily focuses on pathway specific edits and optimization after each round of engineering changes. The resulting strains usually cannot produce more than one particular chemical at high titers due to a need for different engineered pathways. Thus, under the current paradigm, the development pipeline must be started from scratch for each new compound of interest or pathway, which leads to highly siloed strains that are very sensitive to small changes in process conditions like new carbon sources, oxygen levels, or nutrient availability.

Considerable effort has focused on fine-tuning pathway flux and genetic circuits. But pathway improvements typically put heavy burdens on cell growth, which leads to evolutionary pressure to reverse those changes through mutation. This pressure "breaks" the biocatalyst pathway and causes lower process yields, highly variable production, and catastrophic failure of the system when scaling up to industrially relevant volumes.

Removing pathway fragility from a strain is incredibly difficult due to the complexity of the cell stress-response network. There are multiple unknown parameters that dictate the response to perturbations. The natural stochastic sensing of these responses may lead to non-genetic population heterogeneity, which lowers overall productivity. Furthermore, most engineering changes contribute stress to the cell through burdening translational capacity, changing native levels of metabolite pools, or generating toxic intermediates and products. It is a delicate balancing act to make productive pathway changes while maintaining cell health.

Premature execution of hibernation programs interferes with metabolism and engineered pathways. Creating strains that can mitigate these increased stress-loads is vital for a healthy and productive bioprocess. Efforts to increase robustness for issues like redox balance have previously been explored, but global strain improvements were limited to directed evolution for product tolerance, or balancing pathways based on feedback from global stress signals. These attempts were limited in scope, and the system complexity makes it difficult to know how to fix the larger incoherent stress responses. Multiple chassis strains can be screened at initial engineering stages for improved production, but the genetic diversity of the starting strains make it difficult to understand cause and effect and global edits are typically not pursed beyond initial screens.

Stress effectors have complimentary but redundant roles in stress responses. The inactivation of these effectors is complicated, and in some cases dysregulated expression of downstream genes causes loss of fitness and removal of some proteins causes loss of viability in stationary phase. Translation, in particular, appears to be a limiting factor for cell growth. For example, E. coli limit their pool of active ribosomes in response to stress, rather than globally fine-tuning translation rates. This is accomplished using unique strategies in different nutrient deprivation conditions to limit the translational capacity of the cell. Production of complex molecules in rich media is often well below theoretical limits with low bio-productivity even though amino acids, carbon, and nutrients are present in excess, thus indicating that the systems that monitor and shutdown ribosomes can become incorrectly activated in engineered systems, which causes a global downregulation of metabolism.

Prior productive pathway engineering changes cause strain fragility by overloading native stress-sensing systems that become miscalibrated to the cell's newly engineered metabolism. The present inventors, however, discovered that removing components of the native stress-response networks improve bioproduction. Strategic removal of ribosomal stress effectors improves metabolic activity by maintaining translation capacity and by deactivating hibernation programs that remodel the cell for long term survival. Thus, in contrast to previously engineered bacteria and engineering designs, the present disclosure provides robust and stable stains of modified bacteria in which stress pathways have been engineered to reduce the burden on the cells and enhance bioproduction capabilities. Indeed, in some embodiments, the present disclosure provides modified bacteria in which ribosomal stress effectors have been removed. In some embodiments, the present disclosed provides modified bacteria comprising deactivated hibernation programs. In some embodiments, the present disclosure provides modified bacteria in which ribosomal stress effectors have been removed and that comprise deactivated hibernation programs.

Unlike previous bacterial chassis systems in which genetic edits accumulate and move cells further from homeostasis, which causes stress monitoring systems to become incompatible with the cell's new engineered state, the presently disclosed modified bacterial systems have been engineered in a pathway-agnostic manner, thus allowing the bacteria to avoid metabolic shutdown regardless of other pathway-specific editing or modifications. The wide-ranging potential of such strains is exemplified by the stringent response and tested limonene production in strains edited for sensors (e.g., relA and spoT) and effectors (e.g., Type II toxin antitoxins and ribosomal hibernation proteins known to modulate translation). As discussed in further detail in the Examples section below, recombineering of the bacterial sensors and/or effectors increased limonene and shikimate production in strains missing type II TA systems, and the same is expected for disrupted type I TA systems and other compounds of interest that can be synthesized through bioprocessing because the disclosed modified bacteria are engineered in a pathway-agnostic manner to avoid metabolic shutdown regardless of other pathway-specific editing or modifications. Edits involved in the hibernation of ribosomes, such as the deletion of the SOS-associated recA protein, also further improved variance in production and suggests that mutation may be currently limiting the system. Accordingly, in some embodiments, the modified bacteria comprise a deletion of recA (i.e., ΔrecA). In some embodiments, the modified bacteria comprise a deletion of genes encoding type I and/or type II TA systems (e.g., Δ11TA).

A Logical Framework to Remove Stress Effectors, but Keep Sensing Networks Intact To identify targets for general strain improvement, known stress response systems in E. coli were studied. Targeting mechanisms like allostery that are built into metabolic networks as a buffer to perturbations were avoided to move away from pathway "tinkering," since editing metabolic networks directly to reroute flux through pathway bottlenecks is a typical engineering strategy that can be done after a baseline strain is developed. The general logical framework of this plan was to keep stress-sensing networks intact, while removing targeted effectors that carry out unwanted response programs. These effectors shutdown metabolism and are necessary for long-term cell survival. However, cell survival is not an important bioprocess objective once sufficient biomass and catalyst levels are attained, so the present inventors considered these programs were good targets for removal.

Stress Funnels to the Ribosome which Mediates Action Through the Stringent Response During sustained stress, carbon flux is reduced and there is a shortage of RNA and protein precursors, which interrupts transcription and translation due to amino acid starvation. One initial amino acid edit fixed was the ilvG-frameshift mutation in the common MG1655 lab strain. This frameshift mutation causes incoherent regulation of branched chain amino acid synthesis. For global amino acid sensing, the stringent response is an important target. The stringent response is a key stress network that senses amino acid starvation and coordinates ribosome synthesis with amino acid biosynthesis. When uncharged tRNA enter the ribosome active site RelA or SpoT are activated to synthesize guanosine pentaphosphate (ppGpp). ppGpp and the transcription factor DksA interact with RNA polymerase to vastly alter transcription. In parallel, translation is down-regulated through a complex regulatory cascade. The present inventors wanted to avoid editing transcription factors that modulate many gene responses, so dksA was not considered. relA and spoT are gene targets that were suspected to prevent some TA activation by disrupting ppGpp signaling. However, ΔrelA strains have dysregulated RNA and protein synthesis and ppGpp null strains are auxotrophic for multiple amino acids.

ppGpp levels initiate production of several type II Toxin-Antitoxin (TA) systems. These type II TA systems quickly alter translation through a signal cascade; degradation of unstable antitoxins by proteases activates partner toxins which degrade mRNA/rRNA/tmRNA or phosphorylate tRNA-synthetases. Type II TA systems were identified as stringent-response deletions to test. Removal of type II TA systems prevented disruption of translation without changing the large and complex stringent stress-sensing network. Lon protease and polyphosphate pool enzymes are involved in cell-division control and phosphate storage, so these proteins were not targeted edits.

Structural proteins that modulate ribosomes and package them for hibernation are also of interest, as Rmf and SRA are rapidly produced when ppGpp levels rise. Rmf and Hpf work together to package ribosomes into dimers, whereas RsfS, RaiA, and SRA bind to form monosomes in stationary phase. yqjD, elaB, and ygaM are membrane associated proteins that may help sequester ribosomes away from transcriptional machinery. While exact interactions for all these ribosome factors are not known, they generally reduce protein synthesis, which can contribute to metabolic shutdown in direct and indirect ways. Since these proteins may have additional functions, (e.g., RaiA may have proofreading function) it is difficult to predict which edits would improve bioprocesses without making and testing knockouts. Other stress responses that are controlled by the stringent response transcriptional network include: general stress genes for DNA damage (uspAB), cold shock genes (cspAB), osmotic shock (osmBCEY), and flagellar genes (fliDST, flhBAE, cheRBZY).

There is a whole network of di-cyclic GTP signaling that propagate signals for the production of long-term stresses. Many GTPAses directly interact with ppGpp (rsgA, rbgA, era, hflX, ppX obgE, ygdH, lepA). Many have unknown function and some are essential; obgE is known to connect the stringent response to other networks that sense carbon and sugar phosphate stress. This network may help integrate and coordinate all of the stress signals in the cell, and is extremely complex. Therefore, these genes were not targeted, but the downstream effectors that structurally alter the cell can be removed in certain embodiments (e.g., curli, fimbrae, and biofilm genes).

ROS is a Major Result of a Variety of Stressors

Another major source of stress is reactive oxygen species (ROS), which can be generated from normal metabolism, disrupted iron homeostasis, membrane stress, and other sources. Engineering changes can also trigger ROS production directly through unbalanced redox and indirectly through translational or membrane stress. ROS cause direct DNA damage, which activates the SOS response. This response creates a hyper mutable state that may reverse engineering changes. The SOS response cascade is mediated through the LexR transcription factor, activated by RecA, which stops cell division, and activates error-prone DNA repair. Stationary-phase DNA binding proteins that compact DNA are also produced and may contribute to metabolic shutdown. These proteins have ROS quenching activity, and may be deleted in some embodiments.

The lexR regulon includes type I TA systems that may be activated during the SOS response (tisB, hokB, ibsAB, ibsCE, ldrABCD, hokACDE, ghoTS, cbtAB, cptAB, shoB, dinQ, symER, and ralAR). Type I toxins are small, hydrophobic "pore" proteins that disrupt membrane polarization, and may contribute to metabolic shutdown by limiting ATP production. Due to RecA involvement in the SOS response, it is a common edit that limits mutation and improves bioproductivity. Since recA and lexR are global transcription regulators, removal of type I TA and error-prone DNA polymerase components is a more targeted approach to improve production without disrupting a large stress network, similar to removing type II TA's to limit the stringent response.

Indeed, type I TA system proteins interfere with the membrane and proton motive force, and there is evidence of underlying regulation (obg) connected to spoT (one of the ppGpp generating enzymes) This depletes ATP, which likely sends the cell into a quiescent state. Accordingly, in some embodiments, the disclosed modified bacteria may comprise one or more modifications to a type I TA system protein or gene encoding the same. For example, the modification may comprise a mutation, down-regulation, or suppression of tisB, hokB, ibsAB, ibsCE, ldrABCD, hokACDE, ghoTS, cbtAB, cptAB, shoB, dinQ, symER, and ralAR. In some embodiments, the modification may comprise a deletion of tisB (ΔtisB), hokB (ΔhokB), ibsAB (ΔibsAB), ibsCE (ΔibsCE), ldrABCD (ΔldrABCD), hokACDE (ΔhokACDE), ghoTS (ΔghoTS), cbtAB (ΔcbtAB), cptAB (ΔcptAB), shoB (ΔshoB), dinQ (ΔdinQ), symER (ΔsymER), and ralAR (ΔralAR).

ROS also cause protein damage by protein carbonylation, which results in insoluble protein aggregates. These aggregates can nucleate newly translated protein and can activate stress response cascades via envelope stress sensors, and protein folding sensors. There is evidence that this is extremely toxic to cells as insoluble protein aggregates buildup (yeast models). Here, preparing the cell before the onslaught of translation and oxidative stress from engineered pathways proved useful. Expressing protein-folding chaperones or adding heterologous disaggregases, can additionally limit the damage from these stressors. Phasin proteins have known protective qualities against toxic metabolites like triacyl glycerides, and they help quench toxicity in ethanol and propanediol bioproduction. Native heat/cold shock protein members that are produced during the stringent response may also be constitutively expressed in some embodiments. Expressing ROS specific detox proteins like katG and sodB themselves may further protect the cell from damage, and these proteins may be upregulated or constitutively expressed in some embodiments.

Macromolecular Machines and Other Structural Edits

Macromolecular structures like flagellar machinery are unnecessary in a metabolic engineering context and therefore may be removed. Components of flagella machinery are produced in response to localized nutrient limitation and are under stringent-control by at least fliDST, fhBAE, and cheRBZY. There is evidence of leaky expression of flagellar components due to metabolic heterogeneity, which occurs in clonal cultures where imperfect mixing and buildup of acetate leads to different carbon consumption patterns. In a well-mixed bioprocess flagellar machinery is unnecessary and takes up unnecessary membrane real-estate and translation resources to construct, while utilizing energy for movement. Complex structural protein and polymer synthesis pathways are also costly components that use resources and are unnecessary vestiges of long-term cell survival. In some embodiments, one or more of biofilms (hna), curli (csgBA & csgDEFG), fimbrae (fim operon, aidA, tibA), cellulose (bcsE, dgcC) and adhesins (yad, bfp, pap, tpsA) may not be expressed by removing or deleting the necessary encoding genes.

As a result, in some embodiments, a modified bacteria of the present disclosure may comprise one or more modifications to the expression of at least one flagellar gene; at least one gene relating to biofilm production, curli, fimbrae, cellulose, or adhesins; at least one gene involved in di-cyclic GTP signaling; or a combination thereof. Such modification are expected to reduce the activity of a toxin protein or suppresses the effects of a toxin protein and/or decrease stress on the bacterial strain.

In some embodiments, the at least one flagellar gene is fliDSf, flhBAE, cheRABZYW, tar, tsr, trg, or tap. In some embodiments, the at least one gene relating to biofilms is hna, tabA, or wcaF. In some embodiments, the at least one gene relating to curli is csgBA and/or csgDEFG. In some embodiments, the at least one gene relating to fimbrae is fim operon, aidA, or tibA. In some embodiments, the at least one gene relating to cellulose is bcsE or dgcC. In some embodiments, the at least one gene relating to adhesins is yad, bfp, pap, or tpsA.

In some embodiments, the modification relates to the expression of at least one flagellar gene. In some embodiments, the modification relates to the expression of at least one gene relating to biofilm production, curli, fimbrae, cellulose, or adhesins. In some embodiments, the modification relates to the expression of at least one gene involved in di-cyclic GTP signaling. In some embodiments, the modification relates to the expression of at least two of: a flagellar gene; a gene relating to biofilm production, curli, fimbrae, cellulose, or adhesins; and a gene involved in di-cyclic GTP signaling. In some embodiments, the modification relates to the expression of all three of: at least one flagellar gene; at least one gene relating to biofilm production, curli, fimbrae, cellulose, or adhesins; and at least one gene involved in di-cyclic GTP signaling.

In some embodiments, the one or more modifications comprise an up-regulation or down-regulation of the gene(s). In some embodiments, the one or more modifications comprise a down regulation, mutation, or deletion of the gene.

Some embodiments may further comprise a modification to the expression of at least one gene encoding a type I and/or type II toxin-antitoxin (TA) system protein and/or at least one gene encoding a structural protein that modulates ribosomes, wherein the modification reduces the activity of a toxin protein or suppresses the effects of a toxin protein.

Exemplary Embodiments of the Disclosed Modified Bacteria

Embodiment 1

The present disclosure provides modified bacteria comprising a modification to the expression of at least one gene encoding a type I and/or type II toxin-antitoxin (TA) system protein and/or at least one gene encoding a structural protein that modulates ribosomes, wherein the modification reduces the activity of a toxin protein or suppresses the effects of a toxin protein. In some embodiments, the modification comprises a down regulation, mutation, or deletion of the gene. In some embodiments, the bacteria comprises a modification to the expression of at least 2, at least 3, at least four, at least 5, at least 6, at least 7, at least 8, at least 9, at least 10, or at least 11 genes encoding a TA system protein and at least one, at least two, at least three, or at least four gene(s) encoding a structural protein that modulates ribosomes.

In some embodiments, the TA system protein is a type II TA system protein. In some embodiments, the TA system protein is a type I TA system protein. In some embodiments, a gene encoding a type I TA system protein and a gene encoding a type II TA system protein are both modified.

In some embodiments, at least one gene encoding a type I and/or type II TA system protein and at least one gene encoding a structural protein that modulates ribosomes are both modified.

In some embodiments, the bacteria is *Escherichia coli* (*E. coli*). However, other bacteria that are useful in bioprocessing are equally amendable to the disclosed modifications. Other bacteria that may be used include, but are not limited to *C. glutamicum*, *B. subtilis*, *P. putida*, *A. baylyi*, oleaginous *Rhodococcus* sp., *V. nateragens*, *Lactobacillus*, and *M. succinigens*.

In some embodiments, at least 2 (Δ2TA), at least 3 (Δ3TA), at least 4 (Δ4TA), at least 5 (Δ5TA), at least 6 (Δ6TA), at least 7 (Δ7TA), at least 8 (Δ8TA), at least 9 (Δ9TA), at least 10 (Δ10TA), or at least 11 (Δ11TA) genes encoding type I and/or type II TA system proteins are modified (e.g., down regulated or deleted). In some embodiments, the genes encoding type II TA system proteins are selected from mazF (ΔmazF), chpB (ΔchpB), chpBS (ΔchpBS), relBE (ΔrelBE), yefM/yoeB (ΔyefM/yoeB), dinJ (ΔdinJ), yafQ (ΔyafQ), dinJ-yafQ (ΔdinJ-yafQ), yefM (ΔyefM), yoeB (ΔyoeB), higBA (ΔhigBA), prlF (ΔprlF), yhaV (ΔyhaV), prlF-yhaV (ΔprlF-yhaV), yafNO (ΔyafNO), mqsRA (ΔmqsRA), hicAB (ΔhicAB), hip BA (ΔhipA), and yafNOP (ΔyafNOP). In some embodiments, the genes encoding type I TA system proteins are selected from tisB (ΔtisB), hokB (ΔhokB), ibsAB (ΔibsAB), ibsCE (ΔibsCE), ldrABCD (ΔldrABCD), hokACDE (ΔhokACDE), ghoTS (ΔghoTS), cbtAB (ΔcbtAB), cptAB (ΔcptAB), shoB (ΔshoB), dinQ (ΔdinQ), symER (ΔsymER), and ralAR (ΔralAR). In some embodiments, at least one, at least two, or all three of hokB, tisB, and shoB are knocked out.

In some embodiments, mazEFG operon is deleted.

In some embodiments, at least 2, at least 3, at least 4, at least 5, or at least 6 or more genes encoding a structural protein that modulates ribosomes are down regulated or deleted. In some embodiments, the genes encoding a structural protein that modulates ribosomes are selected from the group consisting of rmf (Δrmf), hpf (Δhpf), rsfs (Δrsfs), yqjD (ΔyqjD), elaB (ΔelaB), raiA (ΔraiA), ygaM (ΔygaM), and SRA (ΔSRA).

In some embodiments, the bacteria comprises Δ11TA and/or ΔhpfΔrmf. In some embodiments, the bacteria comprises Δ11TA and ΔhpfΔrmf. In some embodiments, the bacteria comprises Δ11TA and ΔhpfΔrmfΔraiAΔrsfsΔSRA. In some embodiments, the bacteria comprises ΔhpfΔrmfΔraiAΔrsfsΔSRA. In some embodiments, the bacteria comprises Δ11TA and ΔhpfΔrmfΔraiAΔyqjDΔelaBΔygaM. In some embodiments, the bacteria comprises ΔhpfΔrmfΔraiAΔyqjDΔelaBΔygaM. In some embodiments, the bacteria comprises Δ11TA and ΔhpfΔrmf and further comprises any or all of the following deletions: Δrsfs, ΔraiA, ΔSRA, ΔyqjD, Δelab, ΔygaM, ΔrelA, or ΔrecA. In some embodiments, the bacteria comprises ΔhpfΔrmf and further comprises any of the following deletions: Δrsfs, ΔraiA, ΔSRA, ΔyqjD, Δelab, ΔygaM, ΔrelA, or ΔrecA.

In some embodiments, relA is deleted (ΔrelA). In some embodiments, recA is deleted (ΔrecA). In some embodiments, relA is not deleted (ΔrelA). In some embodiments, recA is not deleted (ΔrecA).

In some embodiments, the bacteria comprises Δ11TA and ΔhpfΔrmfΔrecAΔrelA. In some embodiments, the bacteria comprises ΔhpfΔrmfΔrecAΔrelA.

In some embodiments, an ilvG− frameshift mutation is corrected (ilvG+).

In some embodiments, the modified bacteria may further comprise one or more modifications to alter expression of katG and/or sodB.

In some embodiments, the modified bacteria may further comprise one or more modifications to up- or down-regulate at least one general stress gene, at least one cold shock gene, at least one osmotic shock gene, or at least one heat shock gene. In some embodiments, and the modified bacteria may further comprise one or more modifications to remove at least one flagellar gene. In some embodiments, the at least one flagellar gene may be fliDST, flhBAE, cheRABZYW, tar, tsr, trg, or tap.

In some embodiments, the modified bacteria may further comprise one or more modifications to down regulate or remove at least one gene relating to biofilm production, curli, fimbrae, cellulose, or adhesins. In some embodiments, the at least one gene relating to biofilms is hna, tabA, or wcaF. In some embodiments, the at least one gene relating to curli is csgBA and/or csgDEFG. In some embodiments, the at least one gene relating to fimbrae is fim operon, aidA, or tibA. In some embodiments, the at least one gene relating to cellulose is bcsE or dgcC. In some embodiments, the at least one gene relating to adhesins is yad, bfp, pap, or tpsA.

In some embodiments, the bacteria may further comprise one or more modifications to alter genes involved in di-cyclic GTP signaling. In some embodiments, the bacteria has not been modified to alter genes involved in di-cyclic GTP signaling.

The present disclosure and examples show how sequentially removing stringent response related stresses in a bacterial expression system (e.g., E. coli) can significantly improve titers and/or yield of compounds of interest that are expressed in bacterial systems. For instance, the Examples below shows that E. coli can be modified to produce titers of limonene up to 760 mg/L, which is a 75% improvement on past studies, and is above titers from follow up studies that used proteomics to balance pathway levels. Additional edits to prevent mutation can lead to large improvements in minimal media production, which is an industrially relevant culture condition, as shown in the Examples below. Based on the data provided herein, complete knockouts of hibernation and sequestration factors (e.g., Δ11TAΔrmfΔhpfΔrsfsΔraiAΔyqjDΔelaBΔygaM) possess improved titer production and yield, as well as general improvements in minimal media production.

The disclosed modified bacteria are good chassis for improved production of a wide range of products, based on the results of improved limonene production as a difficult test case due to its toxicity. For example, better production of a wide range of terpenoid products that use the mevalonate pathway would result from using the disclosed modified bacteria in the bioprocessing. Production increases should mirror those seen in the Examples section below, with gradually improved production from ΔrelA ΔrecA stains to further improved production in Δ11TA ΔhpfΔrmf ΔrecA strains. Since Type II TAs are involved in amino acid starvation, Δ11TA variant strains will improve bioproduction of amino acids. Furthermore, a full hibernation-factor free strain (Δ11TA ΔhpfΔrmfΔraiAΔrsfsΔyqjDΔelaBΔygaM) will further improve titers. The disclosed modified bacteria strains can also prove useful for stationary phase protein production and are good candidates for cell-free protein production and metabolic engineering efforts. These strains will also pair well with synthetic auxotrophy knockouts (i.e., "non-growth mutations"), which may include, but are not limited to ArgA, AroA, AroB, AroC, AroEec, BioC, CysC, CysD, CysI, CysJ, CysQ, GlnA, GltA, GuaA, HisA, Icd, IcdC, IlvA, LeuB, LysA, MetA, MetF, PanB, PanCec, PdxAJ, PdxB, ProC, PurE, PyrC, SerC, and/or ThrB.

Embodiment 2

Also provided herein are modified bacteria comprising one or more modifications to the expression of at least one flagellar gene; at least one gene relating to biofilm production, curli, fimbrae, cellulose, or adhesins; at least one gene involved in di-cyclic GTP signaling; or a combination thereof, wherein the modification reduces the activity of a toxin protein or suppresses the effects of a toxin protein. In some embodiments, the modified bacteria may be is Escherichia coli (E. coli), but as noted above in Embodiment 1, other bacteria that are useful in bioprocessing are equally amendable to the disclosed modifications. Other bacteria that may be used include, but are not limited to C. glutamicum, B. subtilis, P. putida, A. baylyi, oleaginous Rhodococcus sp., V. nateragens, Lactobacillus, and M. succinigens.

The at least one flagellar gene may include, but is not limited to, fliDST, flhBAE, cheRABZYW, tar, tsr, trg, or tap. The at least one gene relating to biofilms may include, but is not limited to, hna, tabA, or wcaF. The at least one gene relating to curli may include, but is not limited to, csgBA and/or csgDEFG. The at least one gene relating to fimbrae may include, but is not limited to, fim operon, aidA, or tibA. The at least one gene relating to cellulose may include, but is not limited to, bcsE or dgcC. The at least one gene relating to adhesins may include, but is not limited to, yad, bfp, pap, or tpsA.

In some embodiments, the bacteria may comprise only one or more modification(s) that relates to the expression of at least one flagellar gene. In some embodiments, the bacteria may comprise only one or more modification(s) that relates to the expression of at least one gene relating to biofilm production, curli, fimbrae, cellulose, or adhesins. In some embodiments, the bacteria may comprise only one or more modification(s) that relates to the expression of at least one gene involved in di-cyclic GTP signaling.

In some embodiments, the modification(s) relates to the expression of at least two of: a flagellar gene; a gene relating to biofilm production, curli, fimbrae, cellulose, or adhesins; and a gene involved in di-cyclic GTP signaling.

In some embodiments, the modification(s) relates to the expression of all three of: at least one flagellar gene; at least one gene relating to biofilm production, curli, fimbrae, cellulose, or adhesins; and a gene involved in di-cyclic GTP signaling.

In some embodiments, the one or more modifications comprise an up-regulation or down-regulation of the gene(s). In some embodiments, the one or more modifications comprise a down regulation, mutation, or deletion of the gene.

In some embodiments, modified bacteria comprising one or more modifications to the expression of at least one flagellar gene; at least one gene relating to biofilm production, curli, fimbrae, cellulose, or adhesins; at least one gene involved in di-cyclic GTP signaling; or a combination thereof may further comprising a modification to the expression of at least one gene encoding a type I and/or type II toxin-antitoxin (TA) system protein and/or at least one gene encoding a structural protein that modulates ribosomes, wherein the modification reduces the activity of a toxin protein or suppresses the effects of a toxin protein. The further modifications to at least one gene encoding a type I and/or type II TA system protein and/or at least one gene encoding a structural protein that modulates ribosomes can be selected from any of the combinations disclosed and discussed under Embodiment 1 above.

For example, the TA system protein is a type II TA system protein or a type I TA system protein, or, in some embodiment, the further modifications may comprise modifying a gene encoding a type I TA system protein and a gene encoding a type II TA system protein. In some embodiments, at least one gene encoding a type I and/or type II TA system protein and at least one gene encoding a structural protein that modulates ribosomes are both modified.

In some embodiments, relA is deleted (ΔrelA). In some embodiments, recA is deleted (ΔrecA). In some embodiments, an ilvG– frameshift mutation is corrected (ilvG+). In some embodiments, the modified bacteria may further comprise one or more modifications to alter expression of katG and/or sodB.

The present disclosure provides modified bacterial system without pathway specific engineering for improved bioproduction. "Improved bioproduction" refers to increasing titers or yields of a compound or chemical of interest that is synthesized or produces by a modified bacterial cell. For example, "improved bioproduction" includes an increase in titers or yield of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 105%, about 110%, about 115%, about 120%, about 125%, about 130%, about 135%, about 140%, about 145%, about 150%, about 155%, about 160%, about 165%, about 170%, about 175%, about 180%, about 185%, about 190%, about 195%, about 200%, about 205%, about 210%, about 215%, about 220%, about 225%, about 230%, about 235%, about 240%, about 245%, about 250%, about 255%, about 260%, about 265%, about 270%, about 275%, about 280%, about 285%, about 290%, about 295%, or about 300% or more. In some embodiments, the increase in titer or yield may be about 50% to about 100%, about 65% to about 85%, about 75% to about 150%, about 100% to about 200%, or about 50% to about 150%.

Further Embodiments Comprising Additional Mutations

Biofilm formation was observed in Δ11TA strain variants in culture tubes left on the bench top for 24 hours after production ended. Since guanosine pentaphosphate (ppGpp) is still made in these cells because relA and spoT are wildtype, further downstream stringent response modules that macroscopically restructure the cell, like curli/fimbrae/biofilm genes, are potential targets to remove. Indeed, in some embodiments, the modified bacteria comprise a deletion of one or more curli, fimbrae, and/or biofilm genes. Removing type I and/or II TAs and hibernation proteins can prevent the cell from modulating its pool of active ribosomes. In some instances, this could lead to overproduction of heterologous proteins, which often cause insoluble aggregates and generate membrane stress. These stressors may activate the SOS regulon or other mutation programs, and therefore in some embodiments, the modified bacteria comprise deletions of genes encoding Type I TAs and/or genes involved in mutation programs, like error prone polymerases and transposon elements.

For any class of compound of interest that is intended to be produced using the disclosed modified bacteria, specific pathway changes may further enhance titers (e.g., changes or modifications to expression of MVA, DXP, acyl-coA, pyruvate/PEP/AKG). The modified bacteria may additionally comprise modifications to increase expression of efflux pumps or other cellular detoxification systems.

III. Methods of Bioproduction

The present disclosure provides methods or uses of any of the foregoing modified bacteria for bioproduction. The follow provides further, non-limiting descriptions of methods of bioproduction that may utilize the disclosed modified bacteria.

Disclosed herein are methods of producing a compound of interest in a modified bacteria, comprising culturing a modified bacteria that expresses or produces an exogenous compound of interest, wherein the modified bacteria comprises a modification of at least one gene encoding a type I and/or type II toxin-antitoxin (TA) system protein and/or at least one gene encoding a structural protein that modulates ribosomes, as described in Section II above. Also disclosed herein are methods of producing a compound of interest in a modified bacteria, comprising culturing a modified bacteria that expresses or produces an exogenous compound of interest, wherein the modified bacteria comprises one or more modifications to the expression of at least one flagellar gene; at least one gene relating to biofilm production, curli, fimbrae, cellulose, or adhesins; at least one gene involved in di-cyclic GTP signaling; or a combination thereof.

In some embodiments, the modification reduces the activity of a toxin protein or suppresses the effects of a toxin protein. In some embodiments, the one or more modifications comprise an up-regulation or down-regulation of the gene(s). In some embodiments, the one or more modifications comprise a down regulation, mutation, or deletion of the gene.

In some embodiments, the modified bacteria may be is *Escherichia coli* (*E. coli*), but other bacteria that are useful in bioprocessing are equally amendable to the disclosed modifications. Other bacteria that may be used include, but are not limited to *C. glutamicum, B. subtilis, P. putida, A. baylyi*, oleaginous *Rhodococcus* sp., *V. nateragens, Lactobacillus*, and *M. succinigens*.

In some embodiments, the bacteria comprises a modification to the expression of at least 2, at least 3, at least four, at least 5, at least 6, at least 7, at least 8, at least 9, at least 10, or at least 11 genes encoding a TA system protein and at least one, at least two, at least three, or at least four gene(s) encoding a structural protein that modulates ribosomes.

In some embodiments, the TA system protein is a type II TA system protein. In some embodiments, the TA system protein is a type I TA system protein. In some embodiments, a gene encoding a type I TA system protein and a gene encoding a type II TA system protein are both modified.

In some embodiments, at least one gene encoding a type I and/or type II TA system protein and at least one gene encoding a structural protein that modulates ribosomes are both modified.

In some embodiments, at least 2 (Δ2TA), at least 3 (Δ3TA), at least 4 (Δ4TA), at least 5 (Δ5TA), at least 6 (Δ6TA), at least 7 (Δ7TA), at least 8 (Δ8TA), at least 9 (Δ9TA), at least 10 (Δ10TA), or at least 11 (Δ11TA) genes encoding type I and/or type II TA system proteins are modified (e.g., down regulated or deleted). In some embodiments, the genes encoding type II TA system proteins are selected from mazF (ΔmazF), chpB (ΔchpB), chpBS (ΔchpBS), relBE (ΔrelBE), yefM/yoeB (ΔyefM/yoeB), dinJ (ΔdinJ), yafQ (ΔyafQ), dinJ-yafQ (ΔdinJ-yafQ), yefM (ΔyefM), yoeB (ΔyoeB), higBA (ΔhigBA), prlF (ΔprlF), yhaV (ΔyhaV), prlF-yhaV (ΔprlF-yhaV), yafNO (ΔyafNO), mqsRA (ΔmqsRA), hicAB (ΔhicAB), hip BA (ΔhipA), and yafNOP (ΔyafNOP). In some embodiments, the genes encoding type I TA system proteins are selected from tisB (ΔtisB), hokB (ΔhokB), ibsAB (ΔibsAB), ibsCE (ΔibsCE), ldrABCD (ΔldrABCD), hokACDE (ΔhokACDE), ghoTS (ΔghoTS), cbtAB (ΔcbtAB), cptAB (ΔcptAB), shoB (ΔshoB), dinQ (ΔdinQ), symER (ΔsymER), and ralAR (ΔralAR). In some embodiments, at least one, at least two, or all three of hokB, tisB, and shoB are knocked out.

In some embodiments, mazEFG operon is deleted.

In some embodiments, at least 2, at least 3, at least 4, at least 5, or at least 6 or more genes encoding a structural protein that modulates ribosomes are down regulated or deleted. In some embodiments, the genes encoding a structural protein that modulates ribosomes are selected from the group consisting of rmf (Δrmf), hpf (Δhpf), rsfs (Δrsfs), yqjD (ΔyqjD), elaB (ΔelaB), raiA (ΔraiA), ygaM (ΔygaM), and SRA (ΔSRA).

In some embodiments, the bacteria comprises Δ11TA and/or ΔhpfΔrmf. In some embodiments, the bacteria comprises Δ11TA and ΔhpfΔrmf. In some embodiments, the bacteria comprises Δ11TA and ΔhpfΔrmfΔraiAΔrsfsΔSRA. In some embodiments, the bacteria comprises ΔhpfΔrmfΔraiAΔrsfsΔSRA. In some embodiments, the bacteria comprises Δ11TA and ΔhpfΔrmfΔraiAΔyqjDΔelaBΔygaM. In some embodiments, the bacteria comprises ΔhpfΔrmfΔraiAΔyqjDΔelaBΔygaM. In some embodiments, the bacteria comprises Δ11TA and ΔhpfΔrmf and further comprises any or all of the following deletions: Δrsfs, ΔraiA, ΔSRA, ΔyqjD, Δelab, ΔygaM, ΔrelA, or ΔrecA. In some embodiments, the bacteria comprises ΔhpfΔrmf and further comprises any of the following deletions: Δrsfs, ΔraiA, ΔSRA, ΔyqjD, Δelab, ΔygaM, ΔrelA, or ΔrecA. In some embodiments, the bacteria comprises Δ11TA and ΔhpfΔrmfΔrecAΔrelA. In some embodiments, the bacteria comprises ΔhpfΔrmfΔrecAΔrelA.

In some embodiments, relA is deleted (ΔrelA). In some embodiments, recA is deleted (ΔrecA). In some embodiments, relA is not deleted (ΔrelA). In some embodiments, recA is not deleted (ΔrecA).

In some embodiments, the modified bacteria may comprise one or more modifications to down regulate or remove at least one gene relating to biofilm production, curli, fimbrae, cellulose, or adhesins. In some embodiments, the at least one gene relating to biofilms is hna, tabA, or wcaF. In some embodiments, the at least one gene relating to curli is csgBA and/or csgDEFG. In some embodiments, the at least one gene relating to fimbrae is fim operon, aidA, or tibA. In some embodiments, the at least one gene relating to cellulose is bcsE or dgcC. In some embodiments, the at least one gene relating to adhesins is yad, bfp, pap, or tpsA.

The at least one flagellar gene may include, but is not limited to, fliDST, flhBAE, cheRABZYW, tar, tsr, trg, or tap. The at least one gene relating to biofilms may include, but is not limited to, hna, tabA, or wcaF. The at least one gene relating to curli may include, but is not limited to, csgBA and/or csgDEFG. The at least one gene relating to fimbrae may include, but is not limited to, fim operon, aidA, or tibA. The at least one gene relating to cellulose may include, but is not limited to, bcsE or dgcC. The at least one gene relating to adhesins may include, but is not limited to, yad, bfp, pap, or tpsA.

In some embodiments, the bacteria may comprise only one or more modification(s) that relates to the expression of at least one flagellar gene. In some embodiments, the bacteria may comprise only one or more modification(s) that relates to the expression of at least one gene relating to biofilm production, curli, fimbrae, cellulose, or adhesins. In some embodiments, the bacteria may comprise only one or more modification(s) that relates to the expression of at least one gene involved in di-cyclic GTP signaling.

In some embodiments, the modification(s) relates to the expression of at least two of: a flagellar gene; a gene relating to biofilm production, curli, fimbrae, cellulose, or adhesins; and a gene involved in di-cyclic GTP signaling.

In some embodiments, the modification(s) relates to the expression of all three of: at least one flagellar gene; at least one gene relating to biofilm production, curli, fimbrae, cellulose, or adhesins; and at least one gene involved in di-cyclic GTP signaling.

In some embodiments, relA is deleted (ΔrelA). In some embodiments, recA is deleted (ΔrecA). In some embodiments, an ilvG– frameshift mutation is corrected (ilvG+). In some embodiments, the modified bacteria may further comprise one or more modifications to alter expression of katG and/or sodB.

In some embodiments, the exogenous compound of interest is selected from the group consisting of a protein, mevalonate, a terpene, an amino acid, an organic acid, muconate or cis,cis-muconic acid, a fatty acid, amorphadiene, artemisinic acid, a diol, and shikimate. In some embodiments, the terpene is limonene, amorphadiene, taxadiene, bisabolene, famesene, or pinene. In some embodiments, the amino acid is tyrosine. In some embodiments, the organic acid is citric acid, succinic acid, or 3-hydroxypropionic acid. In some embodiments, the diol is 1,4-butanediol or 1,3-propanediol. Other compounds of interest that may be produced according to the disclosed methods include, but are not limited to, hydroxyl-tyrosine and butanol.

The disclosed methods can drastically increase the number of products made at industrially relevant titers for a wide range of important chemicals, biochemicals, and compounds. Moreover, the disclosed methods provide substantial saving in research and development costs, as these methods reduce the need to start from scratch for each metabolic pathway and chemical produced. For instance, limonene, which is a valuable monoterpene that is difficult to create through bioproduction due to challenges like toxicity of pathway intermediates, is currently made from extraction of citrus fruit peels, and artemisinic acid is produced on a commercial scale using yeast. The presently disclosed bacterial and methods of bioprocessing using the bacteria allows for a significantly more efficient and cost-effective means of producing these compounds on a commercial scale.

EXAMPLES

The following examples are given to illustrate the present disclosure. It should be understood, however, that the disclosure is not to be limited to the specific conditions or details described in these examples.

Example 1—Materials and Methods

Media and Chemicals

Luria-Bertani Broth (LB) (Difco, New Jersey, USA) with appropriate antibiotics was used for growth during strain editing and for 1.5% agar plates. MOPS minimal and EZ rich media was prepared or purchased from Teknova (California, USA) and sterilized with a 0.45 μm filter before use. All chemicals were purchased from Sigma Aldrich, (Missouri, USA) unless otherwise noted. Carbon, antibiotic, and inducer working concentrations were: kanamycin (25 mg/mL), chloramphenicol (17 mg/L), ampicillin (100 mg/L), spectinomycin (25 mg/L); arabinose (0.2% w/v), dextrose (0.5 to 1.0% w/v), glycerol (1.0% v/v), sucrose (8.0% w/v); IPTG (0.025 to 1.0 mM) and aTc (100 μg/L) from Promega (Wisconsin, USA). All DNA was purchased from IDT (California, USA).

Culture Conditions

All experiments were started from single colonies that contained the pJBEI-6410 plasmid and were transformed or streak purified from frozen stock on LB+antibiotic plates the day prior. Pre-cultures were inoculated ~16 hours beforehand in 1 mL of media used for the experiment. Limonene production followed Keasling lab protocols: strains were grown at 30° C. in 15 mL cultures tubes with foam tops at 450 in a New Brunswick Scientific Innova44 incubator (New Jersey, USA), with shaking at 250 rpm. Appropriate antibiotics and 1.0% glucose were added to MOPS minimal or EZ rich media day of trial. Cultures were inoculated with a 1 in 100 dilution of preculture. Limonene production trials were induced with 25 μM IPTG (unless specified otherwise) at 4 hours after inoculation, for all experiments. A 10% overlay of dodecane was added following induction for limonene recovery.

Plasmids and Strains

*E. coli* K-12 BW25113 Keio collection gene knockouts were ordered from the Yale *E. coli* Stock Center (Connecticut, USA). Strain MCJ5987 was a kind gift from the Gerdes lab. DHB10 contained the pJBEI6410 limonene plasmid, and was used as a control to benchmark limonene production. T-SACK was a gift from the Court lab. pJBEI-6410 was a gift from Taek Soon Lee (Addgene plasmid #47049). pORTMAGE-2 was a gift from Csaba Pál (Addgene plasmid #72677). pCP20 was obtained from lab stocks. Other strains and plasmids utilized are shown in the Table below.

TABLE 1

| Base Strain | Strain Genotype | Name used |
|---|---|---|
| JW2755-3 | BW25113 Keio ΔrelA | Keio ΔrelA |
|  | Keio ΔrelA ΔspoT | Keio ΔrelA ΔspoT |
| SC30146 | MG1655 ΔmazFΔchpB ΔrelBE ΔyefM/yoeB | Δ4TA |
|  | Δ4 ΔrelA | Δ4 ΔrelA |
|  | Δ4 ΔrelA ΔspoT | Δ4 ΔrelA ΔspoT |
| MCJ5987 | MG1655 ΔmazF*ΔchpBΔrelBEΔ(dinJ-yafQ)Δ(yefM-yoeB)ΔhigBAΔ(prlF-yhaV) ΔyafNO ΔmqsRA ΔhicAB | Δ10TA |
|  | Δ10 ΔhipA |  |
|  | Δ10 ΔrelA ilvG+ | Δ11TA ΔrelA |
|  | Δ10 ΔhipA ΔrelA ilvG+ | Δ11TA Δhpf |
|  | Δ10 ΔhipA Δhpf ((yhbH) ilvG+ | Δ11TA Δrmf |
|  | Δ10 ΔhipA Δrmf ilvG+ | Δ11TA ΔyqjD |
|  | Δ10 ΔhipA ΔyqjD ilvG+ | Δ11TA Δrsfs |
|  | Δ10 ΔhipA Δrsfs (ybeB) ilvG+ | Δ11TA ΔelaB |
|  | Δ10 ΔhipA ΔelaB ilvG+ | Δ11TA ΔhpfΔrmf |
|  |  | Δ10 |
|  | Δ10 ΔhipA ΔyhbH Δrmf ilvG+ | ΔhpfΔrmfΔrecA |
|  | Δ10 ΔhipA ΔyhbH Δrmf ΔrecA ilvG+ |  |
|  | Plasmids |  |
|  | pCP20 |  |
|  | pORTMAGE-2 |  |
|  | pJBEI-6410 |  |

Chromosomal Editing

Recombineering was done with pORTMAGE-2, which contains lambda-red machinery and dominant negative MutL under cI857 temperature repression. The following protocol was used.

Cells with the pORTMAGE-2 plasmid were inoculated in 2-5 mL of LB+amp and grown at 30° C. until 0.6 OD600.

Cells were transferred to a 42° C. water bath for 15 minutes to induce recombineering machinery.

Cells were chilled on ice for 5 minutes, then spun down at 17,000×g for 1 minute.

Cells were washed with 1 mL of ice-cold 10% glycerol, and spun down again. The wash cycle was repeated once, with a final resuspension in 100 µL of a 10% glycerol solution.

DNA for edits was added at a final concentration of 1 ng/µL for oligos and ~10 µg for kan-FRT, spect-FRT or tetA-sacB knockout cassettes.

Cells were electroporated with an Eppendorf porator at 2,500V and immediately recovered in 1 mL of SOC media.

Cells were grown for ~1 hour, then 100 µL of culture was spread on appropriate selection plates, grown at 34° C. to maintain pORTMAGE-2.

Colonies were then streak purified on selection plates, and colony PCR using appropriate primers was used to confirm edits. To remove the kan or spect cassette, colonies were transformed with pCP20, and grown at 34° C. Successful transformants were then inoculated in LB+cm and grown at 34° C. for 2 hours to maintain the plasmid, then diluted into LB for ~6 hours at 40° C. to induce the flip recombinase and remove pCP20. Cells were then streak purified on LB plates and grown at 34° C. overnight. To test for plasmid curing and flip out of the kan cassette, multiple colonies were resuspended, and each was inoculated in LB, LB+amp, LB+cm, and LB+kan or spect. Colonies that only grew in LB were screened with colony PCR to confirm removal of the cassette, and frozen stocks of 25% glycerol were made and stored at −80° C.

Knockout cassettes with gene homology were generated by PCR with overhang homology designed to match the Keio collection. Otherwise, the knockout cassettes were directly PCRed from the genome of the specific Keio collection gene knockout. The spect-FRT cassette with flp- was synthesized from IDT, and used as the template to add overhand homology via PCR. spoT::X strains were generated with a tetA-sacB cassette taken from strain T-SACK, gel purified, and used for PCR template to add homology. Scar sites were removed using recombineering with 500 bp gBlocks from IDT.

Limonene Analysis

Limonene samples were taken every 24 hours for up to 96 hours. To sample, cultures were removed from the incubator and 500 µL of culture was taken after pipetting 10 times to evenly mix and maintain an ~10% dodecane overlay for future samples. 500 µL of saturated sodium chloride was added, vortexed for 10 seconds, then spun down at 17,000×g for 20 minutes to clarify and separate the dodecane layer. Samples from the dodecane layer were diluted between 1/25 to 1/1000 in hexanes containing 5 mg/L of β-caryophyllene as an internal standard. An (r)-limonene standard was diluted in a range of $10^{-6}$ to $10^{-4}$ (v/v) in hexanes+beta-caryophyllene to construct a linear curve for limonene quantification.

Limonene was quantified using an Agilent 7890A Gas Chromatograph with 5977A MSD, running software version 5.03[045] (Agilent, California, USA). An Agilent HP-5MS ultra inert column (30 m length×250 µm i.d.×0.25 µm film) was used for separation with ultra high purity 99.999% helium (Airgas, Pennsylvania, USA) at constant flow of 1 mL/min run in splitless mode. The inlet was set to 120° C., and mass transfer line to 290° C. The following temperature gradient was run: start and held at 70° C. for 0.25 minutes, increased at 40° C./min to 200° C., then increased 30° C./min to 250° C. and held for 0.33 minutes for a total run time of 5.5 minutes. A post-run temperature reached 300° C., and 1 minute equilibration time at 70° C. before the start of the next injection. Injection volume was 1 µL. During the run, the mass spec was off between 0 and 2.3 minutes and from 2.72 to 4 minutes. Mass to charge ratios (m/z) of 40 to 500 were collected. For data processing, files were converted to CDF format and analyzed using Metabolite Detector software to identify compounds, determine retention time alignment across samples, and quantify deconvoluted peaks. Software parameters for quantification were: threshold 10, peak height 5, bin scan 10, and deconvolution width 10. The library for identification was downloaded from the GOLM database. The 136 m/z characteristic ion was used to quantify limonene.

Example 2—Results and Discussion

Parent Strain Benefits from Relaxed Response and Reduced SOS Response

Select genetic edits from the original strains (DH1) used for limonene pathway optimization were explored. It was determined that the ΔrelA edit in the Keio collection background improved limonene titers to ~100 mg/L compared to negligible production from wildtype MG1655, whose low titers were unexpected. This "relaxed" response strain may prevent activation of many stress response modules discussed. Stains with ΔrelA ΔspoT deletions were created to make a ppGpp0 strain. This abolished most limonene production (20 mg/L) and cell lysis was visible in the cultures. Since SpoT is thought to sense carbon and lipid stress, it was postulated that completely removing synthesis of ppGpp prevents beneficial stress responses that are desirable even in bioprocessing. This double knockout causes multiple amino acid auxotrophies and may hurt cell viability when limonene pathway stresses are added to the system. A ΔrelA ΔrecA strain was then created, and it was able to produce a high of 360 mg/L limonene, which was a ~85% recovery of from the original study, indicating these were the causal beneficial deletions in the parent strain. ΔrecA likely works by preventing mutations via two mechanisms: (1) disrupted homologous recombination and (2) stable inactivation of LexR, which continually suppresses the SOS regulon to prevent error prone polymerase mutations involved in SOS DNA repair. Both recA-dependent mechanisms are avenues for mutational escape by cells that could inactivate the limonene pathway and lower titers. Further, the broader SOS response is likely limited which can prevent depletion of ATP levels by inactivating some type I TAs (tisB is part of the lexR regulon). The ΔrelA ΔrecA strain was designated for future pathway studies. However, it was noted that ΔrelA causes a dysregulated RNA/protein ratio phenotype, which wastes cell resources and ΔrecA may prevent some beneficial action of the SOS response network.

Next, the effects of deleting the stringent response sensor/signal-generator (relA) combined with deleting various translational effectors (type II TA systems) were tested. A series of relA and spoT knockouts were constructed in Δ4 TA and Δ10 TA strains and constructed a Δ11TA strain containing the additional hipBA TA deletion. ΔrelAΔspoT and Δ4TA ΔrelAΔspoT strains showed limited production at 0-20 mg/L, so z spoT was not pursued further. The Δ11TA ΔrelA strain outperformed Δ4TA ΔrelA (high of 360 vs 250 mg/L). The Δ11TA strain was chosen for further editing, as ΔrelA was expected to limit improvements.

Removing Hibernation Proteins Improves Titers.

The results from Δ11TA derived strains were used as a basis to further target a class of deletions involved in ribosome hibernation. Knockouts of the known ribosome hibernation modulators were created in the Δ10TA strain, including Δrmf, Δhpf Δrsfs, ΔyqjD, and ΔelaB (ΔraiA and ΔygaM mutants were not recovered). Titer highs in Δrmf, Δhpf and ΔelaB strains were 410, 600, and 460 mg/L, respectively. The Δ11TA Δhpf strain is a 38% improvement on the initial study. There were decreased titers in Δ11TA Δrsfs and ΔyqjD. The next deletion was prioritized as Δrmf from the Δ11TA Δhpf strain, since both strains showed improvement in the first round and there was evidence these proteins partner package ribosomes into 100S polysomes for hibernation. Δ11TA ΔhpfΔrmf showed a high titer of 760 mg/L, with variable production.

Mutational Escape May Cause Variable Bioproductivity

A Δ11TA ΔhpfΔrmfΔrecA strain was constructed to test for improved production and less variable cultures. This slightly lowered titers to 590 mg/L, but showed a high titer of 664 mg/L in minimal MOPs media (after 72 hours). Δ11TA ΔhpfΔrmf grown in minimal media showed large reductions in titer to 160 mg/L. This result and the variable production throughout all the trials indicate that mutational escape was a confounding factor in limonene production. The Δ11TA ΔhpfΔrmfΔrecA strain cultivated in minimal media would drastically lower production costs in an industrial setting compared to using defined rich media.

Improved Bioproduction of Limonene without Pathway Specific Engineering

In this example, limonene titers were improved by sequentially removing stringent response related stresses in $E. coli$. Titers were improved to 760 mg/L, which is a 75% improvement on past studies, and is above titers from follow up studies that used proteomics to balance pathway levels. Additional edits to prevent mutation led to large improvements in minimal media production, which is an industrially relevant culture condition.

Example 3—Shikimate Production

Figure 4:
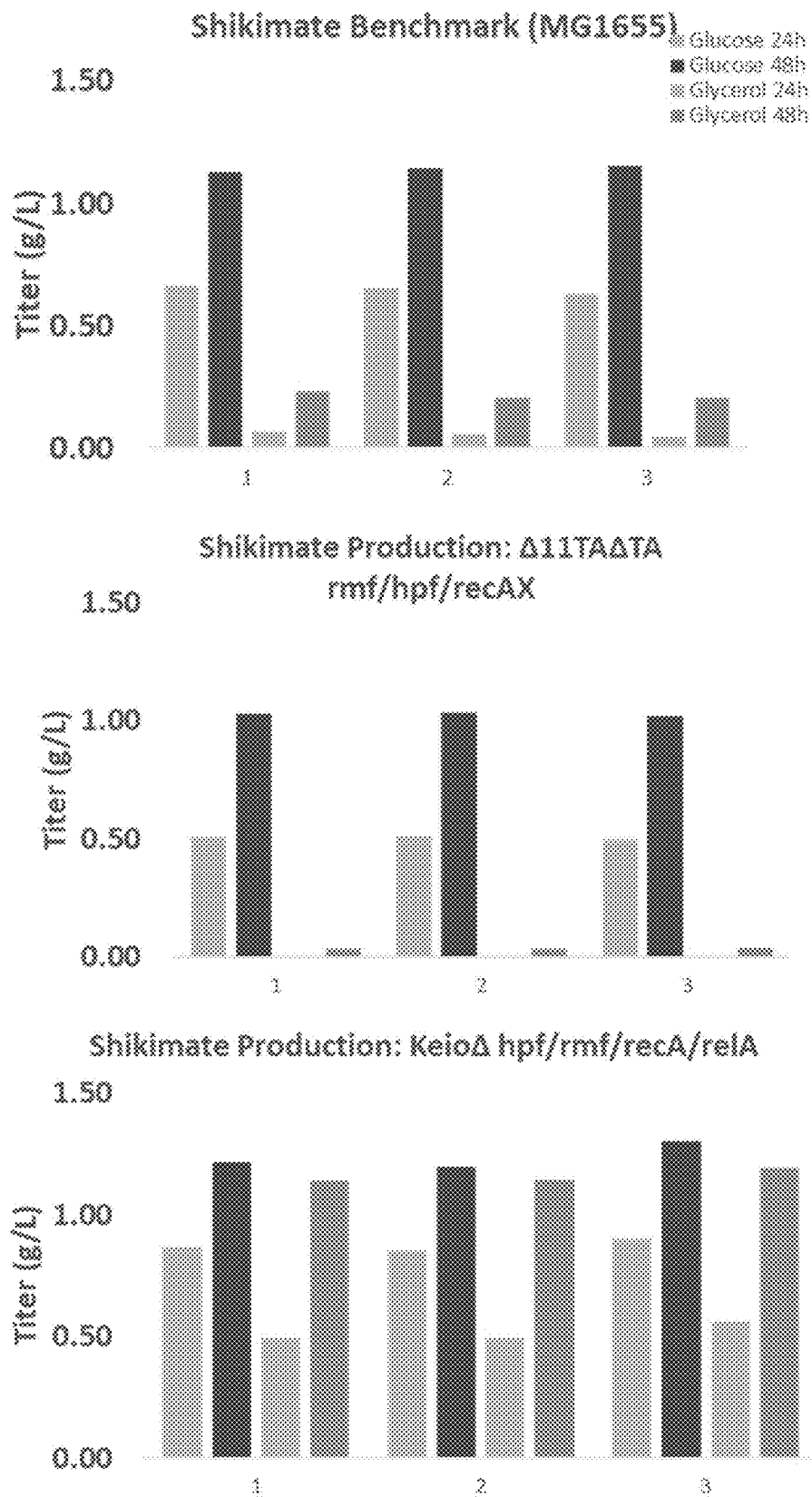
FIG. 4 (FIG. 4) shows shikimate production in modified bacteria strains. The top panel shows a shikimate production benchmark in MG1655 grown in the presence of glucose or glycerol. The middle panel shows shikimate production under the same conditions in Δ11TA ΔhpfΔrmfΔrecA. The bottom panel shows shikimate production under the same conditions in Keio ΔhpfΔrmfΔrecAΔrelA. As seen in the bottom panel, the Keio ΔhpfΔrmfΔrecAΔrelA line provided a 35% increase in shikimate production over the benchmark at 24 hours in glucose and a 10× improvement over the benchmark in the presence of glycerol, as well as the ability to maintain steady production at 48 hours in glycerol.

Similar materials and methods as those described in Example 1 were used to determine the effects of the disclosed bioproduction system on shikimate production. As shown in FIG. 4 below, a significant improvement in shikimate production was observed in Keio ΔhpfΔrmfΔrecAΔrelA. Briefly, The a shikimate plasmids pS3 (pBbB5c::aroE-aroD-aroB$^{op}$-aroG*-ppsA-tktA) was constructed. All EcoRI, BglII, BamHI, and XhoI restriction sites within the sequence were removed from within the ORF by codon substitution. The ORF was amplified by PCR with primers that extended the 5' and 3' ends with EcoRIXXBglII and BamHIXXXhoI, respectively. Positions XX were the adenylate dinucleotides (AA) but could be any random sequence. Similar to the other ORFs in this study, all genes contained the consensus 5'-AGGAGG-3' ribosome binding site (RBS) followed by a spacer sequence, 5'-CCATCC-3'. Prior to cloning, all PCR fragments were digested with BglII and XhoI and then inserted into the corresponding plasmid stepwise, from the 5' end to the 3' end, replacing the original insert, gfp or rfp, respectively. The pS3 plasmid was a result of stepwise alterations, from a pSC101 cloning vector in which pS1 replaced the pSC101 origin and the promoter $P_{LtetO-1}$ on pS0 with the pBBR1 origin and $P_{lac-uv5}$, respectively; pS2 replaced aroB on pS1 with its codon-optimized variant, aroB$^{op}$; and, finally, pS3 replaced ydiB on pS2 with aroE.

Example 4—Limonene Production Under Various Conditions

Figure 5:
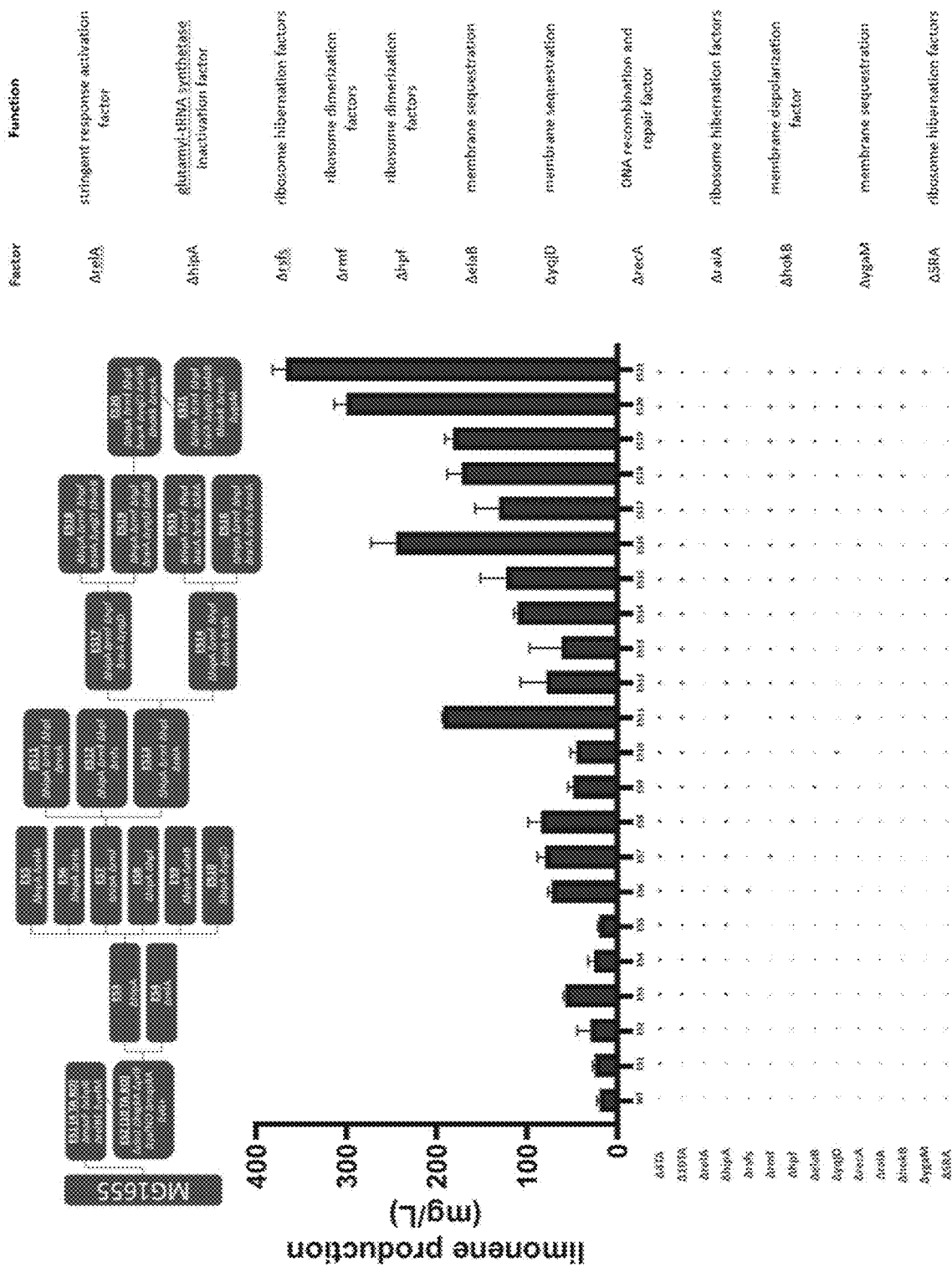
FIG. 5 (FIG. 5) shows a flowchart of strain construction. Production titers of all constructed strains under shake flask conditions for 72 h with EZ rich media and 2% glucose. Table showing ribosome homeostasis modulation factors.
Figure 6:
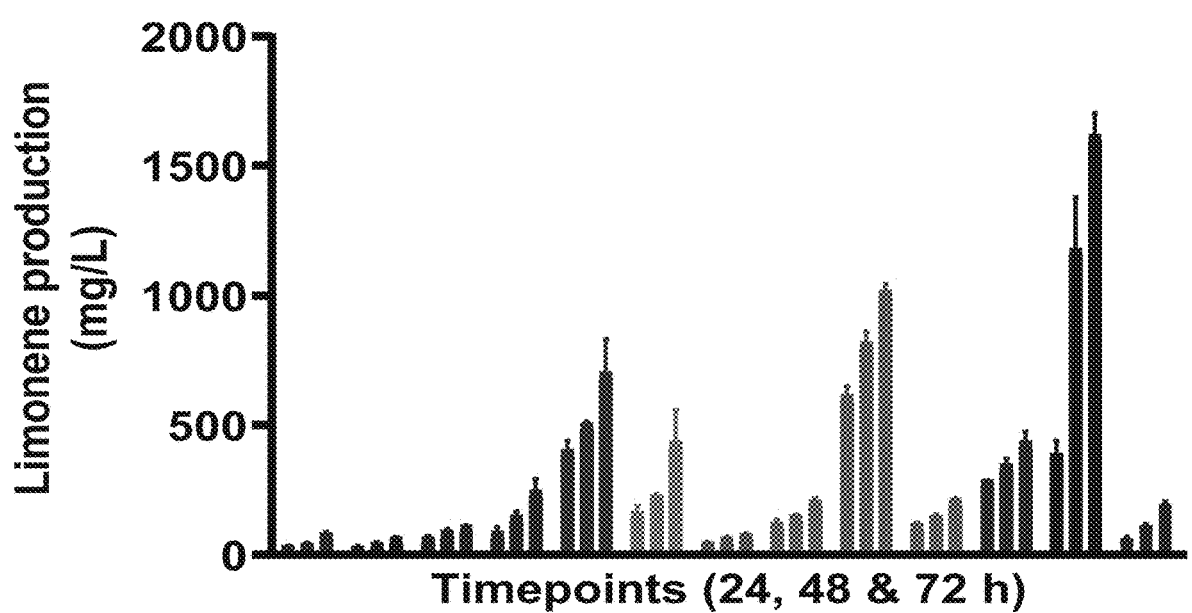
FIG. 6 (FIG. 6) shows production titers of selected strains showing continual limonene production over 24, 48 and 72 h under shake flask conditions and EZ rich media with 2% glucose.
Figure 7:
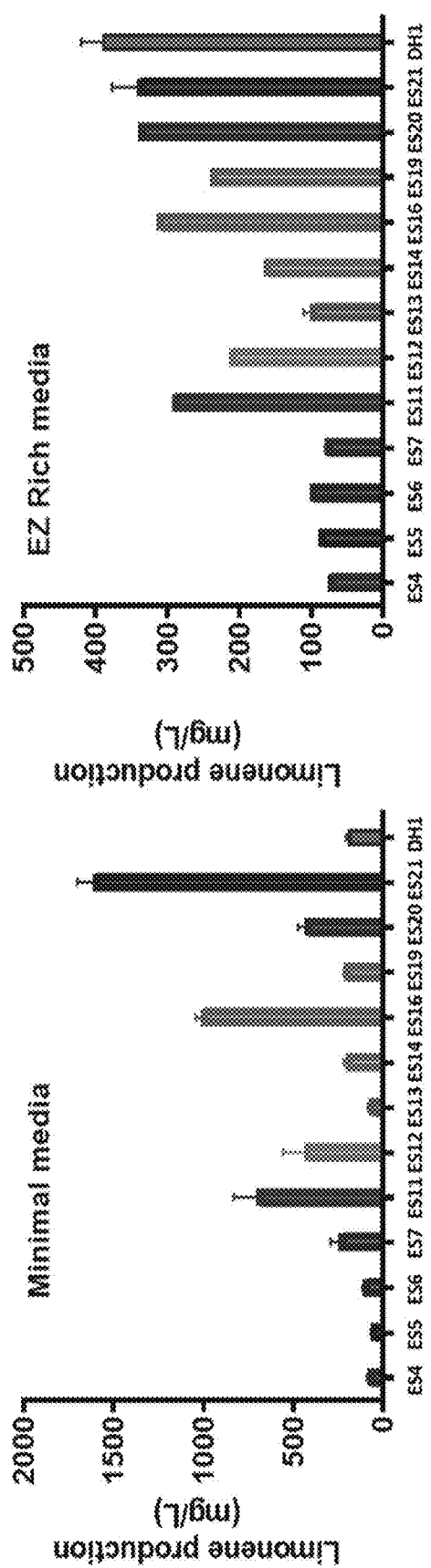
FIG. 7 (FIG. 7) shows production titers of selected strains showing limonene production over 72 h under shake flask conditions with 2% glucose in minimal media or EZ rich media. Minimal media production is far greater than production in EZ rich media.
Figure 8:
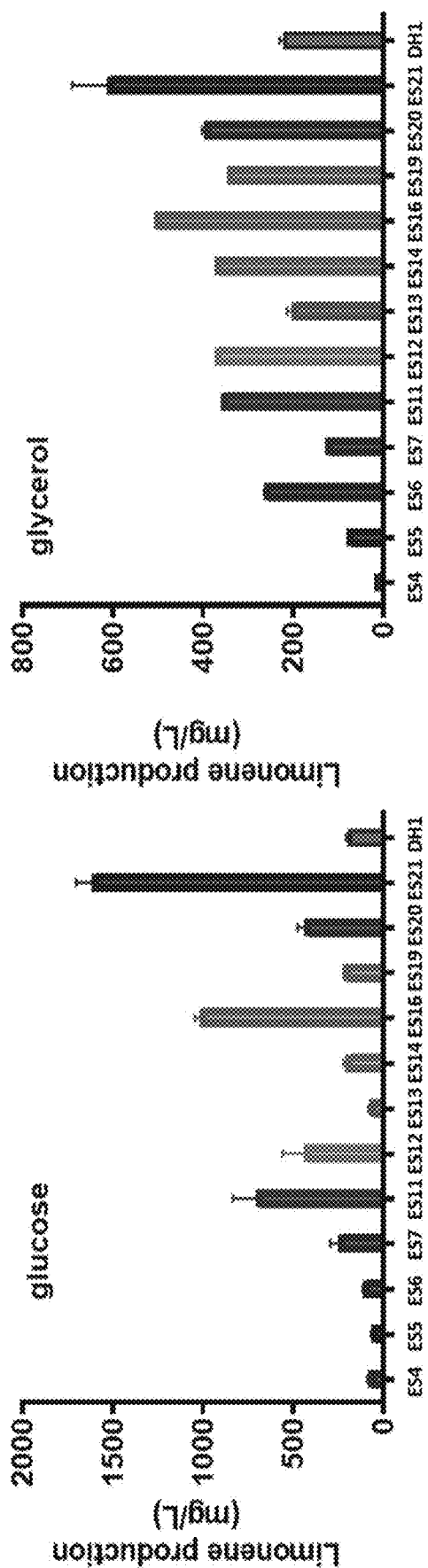
FIG. 8 (FIG. 8) shows production titers of selected strains showing limonene production over 72 h under shake flask conditions minimal media and 2% carbon source of either glucose or glycerol.

Similar materials and methods as those described in Example 1 were used to determine the effects of the disclosed bioproduction system on limonene production under various culture conditions. Namely, baseline limonene production was established for selected strains at 24, 48, and 72 hours (see FIGS. 5 and 6). Thereafter, different media and carbon sources were assessed. First, selected strains were grown under shake flask conditions with 2% glucose in either minimal media or EZ rich media. Limonene production was assessed at 72 hours. Interestingly, limonene production was far greater in minimal media (FIG. 7). Next, selected strains were grown under shake flask conditions in minimal media supplemented with either 2% glucose or 2% glycerol. In general, glucose appeared to be the better carbon source (FIG. 8). A listing of the selected strains that were utilized for these comparative experiments is provided in FIG. 9.

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

One skilled in the art readily appreciates that the present disclosure is well adapted to carry out the objects and obtain the ends and advantages mentioned, as well as those inherent therein. Modifications therein and other uses will occur to those skilled in the art. These modifications are encompassed within the spirit of the disclosure and are defined by the scope of the claims, which set forth non-limiting embodiments of the disclosure.

In addition, where features or aspects of the disclosure are described in terms of Markush groups, those skilled in the art will recognize that the disclosure is also thereby described in terms of any individual member or subgroup of members of the Markush group.

What is claimed:

1. A modified bacterium comprising a modification to the expression of at least ten genes encoding a type I or type II toxin-antitoxin (TA) system protein (Δ10TA) wherein the modification reduces the activity of a toxin protein or suppresses the effects of a toxin protein, and at least two genes encoding structural proteins that modulate ribosomes selected from rmf (Δrmf), hpf (Δhpf), rsfs (Δrsfs), yqjD (ΔyqjD), elaB (ΔelaB), raiA (ΔraiA), ygaM (ΔygaM), and SRA (ΔSRA), wherein the bacterium is $Escherichia coli$ ($E. coli$).

2. The modified bacterium of claim 1, wherein the at least ten genes encode a type II TA system protein.

3. The modified bacterium of claim 1, wherein the at least ten genes encode a type I TA system protein.

4. The modified bacterium of claim 1, wherein a gene encoding a type I TA system protein and a gene encoding a type II TA system protein are both modified.

5. The modified bacterium of claim 1, wherein at least eleven genes encoding a type I or type II TA system protein are modified and at least two genes encoding structural proteins that modulate ribosomes are both modified.

6. The modified bacterium of claim 1, wherein the modification comprises a down regulation, mutation, or deletion of the gene.

7. The modified bacterium of claim 1, wherein the bacterium comprises modifications to the expression of at least ten genes encoding a TA system protein and at least two genes encoding structural proteins that modulate ribosomes.

8. The modified bacterium of claim 1, wherein at least 4 (Δ4TA) genes encoding TA system proteins are deleted.

9. The modified bacterium of claim 1, wherein the at least one gene encoding a type II TA system protein is selected from mazF(ΔmazF), chpB (ΔchpB), chpBS (ΔchpBS), relBE (ΔrelBE), yefM/yoeB (ΔyefM/yoeB), dinJ (ΔdinJ), yafQ (ΔyafQ), dinJ-yafQ (ΔdinJ-yafQ), yefM (ΔyefM), yoeB(ΔyoeB), higBA (ΔhigBA), prlF (ΔprlF), yhaV (ΔyhaV), prlF-yhaV (ΔprlF-yhaV), yafNO (ΔyafNO), mqsRA (ΔmqsRA), hicAB (ΔhicAB), hip BA (ΔhipA), and yafNOP (ΔyafNOP) is modified.

10. The modified bacterium of claim 1, wherein the at least one gene encoding a type I TA system protein is selected from tisB (ΔtisB), hokB (ΔhokB), ibsAB (ΔibsAB), ibsCE (ΔibsCE), IdrABCD (ΔldrABCD), hokACDE (ΔhokACDE), ghoTS (ΔghoTS), cbtAB (ΔcbtAB), cptAB (ΔcptAB), shoB (ΔshoB), dinQ (ΔdinQ), symER (ΔsymER), and ralAR (ΔralAR) is modified.

11. The modified bacterium of claim 10, wherein at least hokB, tisB, and shoB are knocked out.

12. The modified bacterium of claim 1, wherein mazEFG operon is deleted.

13. The modified bacterium of claim 1, wherein the at least 2 genes encoding structural proteins that modulate ribosomes are deleted.

14. The modified bacterium of claim 1, wherein the bacterium comprises Δ11TA and ΔhpfΔrmf.

15. The modified bacterium of claim 14, wherein the bacterium comprises Δ11TA and ΔhpfΔrmf and at least 4 (Δ4TA) genes encoding TA system proteins are deleted.

16. The modified bacterium of claim 1, wherein the bacterium comprises:

(i) Δ11TA and ΔhpfΔrmfΔraiAΔrsfsΔSRA;
(ii) ΔhpfΔrmfΔraiAΔrsfsΔSRA;
(iii) ΔhpfΔrmf ΔraiAΔyqjDΔelaBΔygaM;
(iv) ΔhpfΔrmf ΔraiAΔyqjDΔelaBΔygaM;
(v) Δ11TA and ΔhpfΔrmf and further comprises at least one of the deletions selected from Δrsfs, ΔraiA, ΔSRA, ΔyqjD, Δelab, ΔygaM, ΔrelA, and ΔrecA;
(vi) ΔhpfΔrmf and further comprises at least one of the deletions selected from Δrsfs, ΔraiA, ΔSRA, ΔyqjD, Δelab, ΔygaM, ΔrelA, and ΔrecA;
(vii) Δ11TA and ΔhpfΔrmfΔrecAΔrelA; or
(viii) ΔhpfΔrmfΔrecAΔrelA.

17. The modified bacterium of claim 1, wherein relA is deleted (ΔrelA), recA is deleted (ΔrecA), or a combination thereof.

18. The modified bacterium of claim 1, wherein an ilvG-frameshift mutation is corrected (ilvG+).

19. The modified bacterium of claim 1 further comprising one or more modifications to alter expression of katG and/or sodB.

20. The modified bacterium of claim 1 further comprising one or more modifications to up- or down-regulate at least one general stress gene, at least one cold shock gene, at least one osmotic shock gene, or at least one heat shock gene, and remove at least one flagellar gene.

21. The modified bacterium of claim 20, wherein the at least one flagellar gene is fliDST, flhBAE, cheRABZYW, tar, tsr, trg, or tap.

22. The modified bacterium of claim 1 further comprising one or more modifications to down regulate or remove at least one gene relating to biofilm production selected from hna, tabA, or wcaF; at least one gene relating to curli selected from csgBA and csgDEFG; at least one gene relating to fimbrae selected from fim operon, aidA, and tibA; at least one gene relating to cellulose selected from bcsE and dgcC; or at least one gene relating to adhesins selected from yad, bfp, pap, and tpsA.

23. The modified bacterium of claim 1, wherein the bacterium has been modified to alter genes involved in di-cyclic GTP signaling.

24. The modified bacterium of claim 1, wherein the bacterium has not been modified to alter genes involved in di-cyclic GTP signaling.

25. A method of producing a compound of interest in a modified bacteria, comprising culturing a modified bacteria according to claim 1 that expresses or produces an exogenous compound of interest.

* * * * *